US011933477B2

(12) United States Patent
Childress et al.

(10) Patent No.: US 11,933,477 B2
(45) Date of Patent: Mar. 19, 2024

(54) SYSTEMS AND METHODS FOR ALIGNING ULTRAVIOLET LAMPS

(71) Applicant: THE BOEING COMPANY, Chicago, IL (US)

(72) Inventors: Jamie J. Childress, Mercer Island, WA (US); Arthur Edward Brockschmidt, Jr., Renton, WA (US)

(73) Assignee: The Boeing Company, Chicago, IL (US)

( * ) Notice: Subject to any disclaimer, the term of this patent is extended or adjusted under 35 U.S.C. 154(b) by 492 days.

(21) Appl. No.: 17/347,905

(22) Filed: Jun. 15, 2021

(65) Prior Publication Data

US 2022/0113006 A1    Apr. 14, 2022

Related U.S. Application Data

(60) Provisional application No. 63/118,035, filed on Nov. 25, 2020, provisional application No. 63/091,444, filed on Oct. 14, 2020.

(51) Int. Cl.
| *F21V 14/02* | (2006.01) |
| *A61L 2/10* | (2006.01) |
| *F21V 21/22* | (2006.01) |
| *F21V 23/06* | (2006.01) |
| *G01J 1/42* | (2006.01) |

(52) U.S. Cl.
CPC ............ *F21V 14/02* (2013.01); *A61L 2/10* (2013.01); *F21V 21/22* (2013.01); *G01J 1/429* (2013.01); *F21V 23/06* (2013.01)

(58) Field of Classification Search
CPC .......... F21V 14/02; F21V 21/22; F21V 23/06; A61L 2/10; A61L 2202/14; A61L 2202/16; A61L 2209/111; A61L 9/20; A61L 2202/25; G01J 1/429
See application file for complete search history.

(56) References Cited

U.S. PATENT DOCUMENTS

2013/0330235 A1    12/2013  Stibich
2018/0339075 A1*   11/2018  Kennedy .................. A61L 2/24
(Continued)

FOREIGN PATENT DOCUMENTS

JP        2000 283840     10/2000
WO    WO 2012/142427     10/2012

OTHER PUBLICATIONS

U.S. Appl. No. 17/016,466, filed Sep. 10, 2020.
(Continued)

*Primary Examiner* — David P Porta
*Assistant Examiner* — Meenakshi S Sahu
(74) *Attorney, Agent, or Firm* — Joseph M. Butscher; The Small Patent Law Group, LLC

(57) ABSTRACT

A system and method for verifying a desired alignment of an ultraviolet (UV) lamp with respect to a target component include a housing. A UV sensor is coupled to the housing. The UV sensor is configured to detect UV light emitted from one or more UV light emitters of the UV lamp and output one or more signals indicative of the UV light. A UV recorder is coupled to the housing. The UV recorder is in communication with the UV sensor. The UV recorder is configured to receive the one or more signals from the UV sensor and store data regarding the one or more signals.

20 Claims, 26 Drawing Sheets

(56) References Cited

U.S. PATENT DOCUMENTS

2022/0111086 A1* 4/2022 Childress .................. A61L 9/20
2022/0111096 A1* 4/2022 Childress .................. A61L 2/26
2022/0184253 A1* 6/2022 Childress .................. A61L 2/24

OTHER PUBLICATIONS

U.S. Appl. No. 29/735,235, filed May 19, 2020.
U.S. Appl. No. 17/039,011, filed Sep. 30, 2020.
U.S. Appl. No. 17/026,414, filed Sep. 21, 2020.
U.S. Appl. No. 17/020,942, filed Sep. 15, 2020.
U.S. Appl. No. 16/987,514, filed Aug. 7, 2020.
U.S. Appl. No. 17/104,628, filed Nov. 25, 2020.
U.S. Appl. No. 16/987,647, filed Aug. 7, 2020.
U.S. Appl. No. 17/026,417, filed Sep. 21, 2020.
U.S. Appl. No. 17/020,951, filed Sep. 15, 2020.

"Honeywell UV Treatment System," https://aerospace.honeywell.com/en/learn/products/cabin/uv-cabin-system.
U.S. Appl. No. 17/026,435, filed Sep. 21, 2020.
U.S. Appl. No. 17/022,392, filed Sep. 16, 2020.
Extended European Search Report for EP App. No. 21210410.3-1020, dated Apr. 25, 2022.
"UVC Sensors to Monitor Ultraviolet Germicidal Irradiation (UVGI)", Jan. 2, 2019, pp. 1-2, retried from the Internet: URL:https://www.pro-lite.co.uk/File/Solar%20Light%20UVGI%20Radiometer%20Brochure.pdf.
Barrett: "Sterilization of sea lice eggs with ultraviolet C light: towards a new preventative technique for aquaculture", Pest Management Science, vol. 76, No. 3, Oct. 3, 2019, pp. 901-906.
Huang: "Research on UV radiation measurements and correction methods", International Symposium on Photolectronic Detection and Imaging 2011: Laser sensing and imaging; and biological and medical applications of photonics sensing and imaging, SPIE, 1000 20th St. Bellingham WA 98225-6705, vol. 8192, No. 1, Jun. 9, 2011.

* cited by examiner

SYSTEMS AND METHODS FOR ALIGNING ULTRAVIOLET LAMPS

RELATED APPLICATIONS

This application relates to and claims priority benefits from U.S. Provisional Patent Application No. 63/118,035, entitled "Systems and Methods for Aligning Ultraviolet Lamps," filed Nov. 25, 2020, which is hereby incorporated by reference in its entirety.

This application also relates to U.S. Provisional Patent Application No. 63/091,444, entitled "Ultraviolet Light Sanitizing Systems and Methods," filed Oct. 14, 2020, which is hereby incorporated by reference in its entirety.

FIELD OF THE DISCLOSURE

Embodiments of the present disclosure generally relate to ultraviolet (UV) light sanitizing systems, such as may be used to sanitize structures and areas within vehicles, and more particularly to systems and methods for aligning UV lamps of the UV light sanitizing systems.

BACKGROUND OF THE DISCLOSURE

Vehicles such as commercial aircraft are used to transport passengers between various locations. Systems are currently being developed to disinfect or otherwise sanitize surfaces within aircraft, for example, that use ultraviolet (UV) light.

A UV light sanitizing system typically includes a UV lamp that includes a plurality of UV light emitters. The UV lamp is formed by integrating the various UV light emitters into a single housing and coupling the UV light emitters to a separate power supply.

When a UV light sanitizing system is installed at a location, such as within a lavatory of an internal cabin of a vehicle, one or more UV lamps of the system need to be aligned to ensure a desired amount of UV illumination at a target surface. However, certain locations include occupancy sensors that preclude an installation technician from being therein when UV light is emitted. For example, certain lavatories within aircraft include sensors that prevent UV lamps from emitting UV light when the lavatories are occupied.

In such a setting, a UV light irradiance meter typically cannot be read directly when during testing. A meter would need to be placed in a targeted location, and then an installation technician would leave the room to illuminate the light and record the reading. However, the system may not be well aligned, thereby requiring the installation technician to make adjustments based upon an estimate of the alignment and retest.

As can be appreciated, such an alignment process may not allow for adequate validation of desired UV illumination, irradiance, and alignment of UV light emitters of a UV lamp.

SUMMARY OF THE DISCLOSURE

A need exists for a system and a method of aligning a UV lamp within a setting that may not allow for an individual to be present.

With that need in mind, certain embodiments of the present disclosure provide a system for verifying a desired alignment of an ultraviolet (UV) lamp with respect to a target component. The system includes a housing. A UV sensor is coupled to the housing. The UV sensor is configured to detect UV light emitted from one or more UV light emitters of the UV lamp and output one or more signals indicative of the UV light. A UV recorder is coupled to the housing. The UV recorder is in communication with the UV sensor. The UV recorder is configured to receive the one or more signals from the UV sensor and store data regarding the one or more signals.

In at least one embodiment, the system also includes a pointer extending from the housing. The pointer is configured to assist in aligning the UV sensor with the one or more UV light emitters. As an example, the pointer is movable between a retracted position and an extended position. As a further example, the pointer is configured to linearly move between the retracted position and the extended position. As a further example, the pointer is a telescoping arm having a plurality of telescoping segments.

In at least one embodiment, the system also includes a battery or is otherwise connectable to a power source.

In at least one embodiment, the system also includes a stand connected to the housing. For example, the stand includes a base, and a connection joint that connects to the housing. The connection joint allows the housing to move relative to the stand.

In at least one embodiment, the UV recorder comprises a control unit that receives the one or more signals.

Certain embodiments of the present disclosure provide a method for verifying a desired alignment of an ultraviolet (UV) lamp with respect to a target component. The method includes detecting, by a UV sensor coupled to a housing, UV light emitted from one or more UV light emitters of the UV lamp; outputting, by the UV sensor, one or more signals indicative of the UV light; receiving, by a UV recorder coupled to the housing and in communication with the UV sensor, the one or more signals from the UV sensor; and storing, by the UV record, data regarding the one or more signals.

Certain embodiments of the present disclosure provide an enclosed space including a target component, an ultraviolet (UV) lamp including one or more UV light emitters, and a system for verifying a desired alignment of the UV lamp with respect to the target component, as described herein.

DETAILED DESCRIPTION OF THE DISCLOSURE

Figure 1:
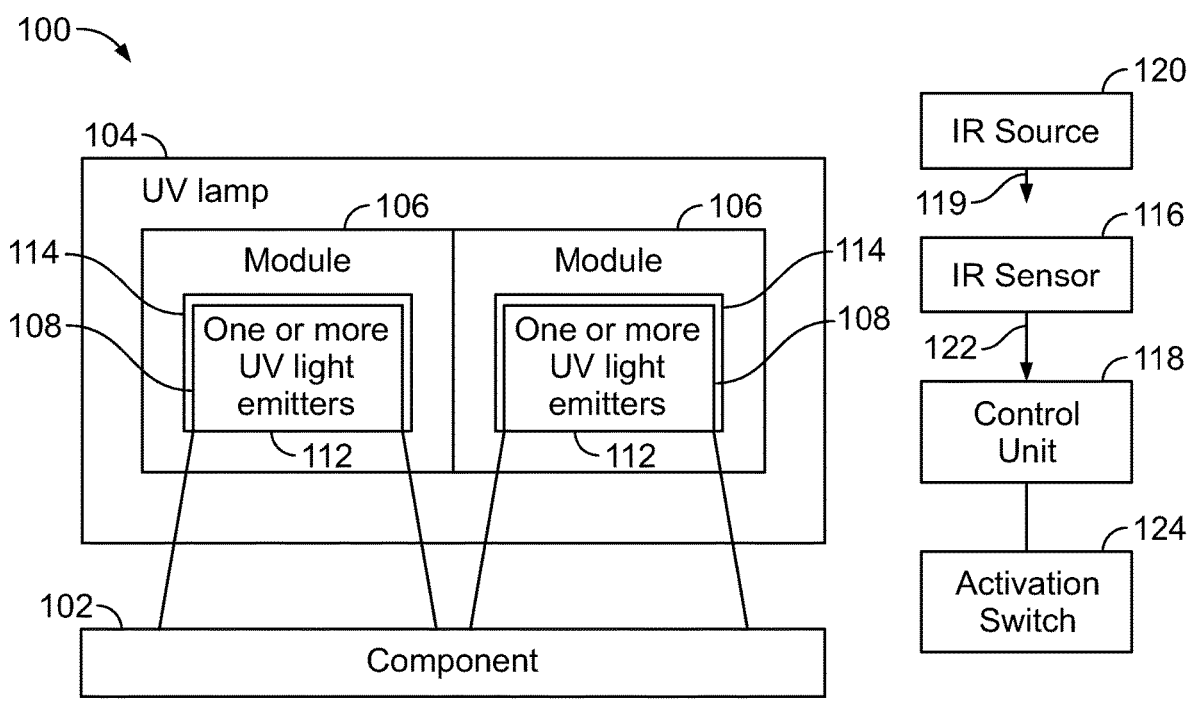
FIG. 1 illustrates a schematic block diagram of a system for disinfecting a component, according to an embodiment of the present disclosure.

The foregoing summary, as well as the following detailed description of certain embodiments will be better understood when read in conjunction with the appended drawings. As used herein, an element or step recited in the singular and preceded by the word "a" or "an" should be understood as not necessarily excluding the plural of the elements or steps. Further, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular condition can include additional elements not having that condition.

Certain embodiments of the present disclosure provide a system for disinfecting (for example, sanitizing, decontaminating, cleaning, or the like) one or more components. The system includes a plurality of modules coupled together to form a UV lamp. Each of the plurality of modules includes one or more UV light emitters that are configured to emit UV light onto a component to disinfect the component. In at least one embodiment, each of the modules also includes a power supply coupled to the UV light emitters. The modules can also include a band pass filter that is configured to filter the generated UV light from the UV light emitters to a desired wavelength, such as within the far UV spectrum, the UVC spectrum, or the like. In at least one embodiment, different modules can emit UV light at different wavelengths. For example, a first module can emit UV light within the far UV spectrum, while a second module coupled to the first module can emit UV light within the UVC spectrum.

Multiple modules may be coupled together (for example, stacked, ganged, or otherwise connected together) as desired for a greater area of UV coverage. Such configuration can be determined based on the size of the surface to be sanitized.

The modules can be coupled together through bonding, one or more mechanical connectors or fasteners, and/or the like.

The UV lamp formed by multiple modules can be customized to fit into desired areas. As such, the UV lamp can be compact and configured to fit into small, confined spaces.

Optionally, the system may not include a plurality of modules. Instead, a single UV lamp having a plurality of UV light emitters can be used with embodiments of the present disclosure.

In at least one embodiment, the UV lamp is part of a wand assembly that is configured to be held by an operator. In at least one other embodiment, the UV lamp is a fixture within a space, such as within a lavatory. The UV lamp can be fixed in position within the space. Optionally, the UV lamp can be configured to be moved between a stowed position and a deployed position within the space. As another option, the UV lamp can be removably secured to a securing mount.

In at least one embodiment, the system includes an infrared (IR) sensor in communication with a control unit. The IR sensor is configured to detect IR light, such as a beam of IR light emitted from an IR source, which can be reflected to the IR sensor. In operation, the control unit is also in communication with the one or more UV light emitters. The control unit is configured to selectively activate and deactivate the UV light emitters in response to a signal received from the IR sensor. For example, the control unit prevents activation of the UV light emitters and/or deactivates the UV light emitters in response to the IR sensor not detecting the IR light.

For example, an IR source and/or an IR reflector can be positioned within a location, such as proximate to (for example, on or within a foot or less) a lavatory door. The IR sensor is configured to monitor the IR beam and to detect a change when an occupant crosses a threshold. Additionally the system can include a door sensor (such as a door hall effect sensor) installed on and/or proximate to the door to detect when the door is open or closed. The control unit can also be in communication with the door sensor and is configured to selectively activate and deactivate the UV light emitters in response to one or more IR signals received from the IR sensor and/or the door sensor.

In at least one embodiment, the control unit is configured to deactivate the UV light emitters when an area (such as a lavatory) is occupied, and to activate the UV light emitters when the area is unoccupied. Integrating the IR sensor into the UV lamp reduces cost and installation time.

Certain embodiments of the present disclosure provide a sanitizing system and method that includes an ultraviolet (UV) lamp (such as an excimer lamp having one or more UV light emitters, such as light emitting diodes, bulbs, and/or the like) that emits UV light in a far UV light spectrum, such as at a wavelength of 222 nm, which neutralizes (such as kills) microbes (for example, viruses and bacteria), while posing no risk to humans. Optionally, the UV lamp emits the UV light in the UVC spectrum, such as at a wavelength of 254 nm. The UV lamp may be used within an internal cabin to decontaminate and kill pathogens. The UV lamp may be used in a portable sanitizing system or a fixed sanitizing system. For example, operating the UV lamp to emit sanitizing UV light having a wavelength within the far UV spectrum or UVC spectrum may be used with a portable system or a fixed system.

Certain embodiments of the present disclosure provide an alignment test system that ensures proper alignment of UV lamps, such as in spaces that are to be unoccupied during testing. The alignment is used to ensure a proper UV illumination with respect to a target. The alignment systems and methods allow an individual (such as an installation technician testing a UV system) to leave a room having a UV lamp while the alignment system validates that the UV light emitters of the UV lamp are in a desired alignment to provide a desired UV radiance in relation to a target component.

In at least one embodiment, the system includes a UV sensor, an attachable base, and an extendable element to ensure proper alignment prior to activating the UV lamp. The alignment system allows for the UV lamp to be aligned as desired after a first test, in contrast to a trial and error approach. As such, the alignment systems and methods reduce installation and testing times, and improve disinfecting UV irradiance in relation to a component.

Certain embodiments of the present disclosure provide an alignment test system to verify a UV lamp is providing a correct UV illumination to a targeted surface. The alignment system includes a housing that contains a UV sensor, a UV recorder, a rechargeable battery, and an extendable pointer. The alignment system can also include a stand attached to the housing, and a weighted base. In at least one embodiment, the stand includes a ball joint or other rotational joint to allow rotation of the housing. The base may also include a suction cup or nonpermanent sticky tape to facilitate stability of the base. The alignment systems and methods are particularly well-suited for spaces that have an occupancy sensor that prevents UV illumination when occupied.

In at least one embodiment, the alignment system is placed on an object or surface to record the UV irradiance emitted from a UV lamp. The pointer is extended to ensure alignment of the UV sensor with the UV lamp. The operator may then turn on the UV recorder and exit the area. The UV light turns on once the room/area is not occupied. The UV sensor detects the intensity of UV radiation and connects to the recorder to output the electrical signal which varies with the UV intensity. In at least one embodiment, the sensor is powered by a microprocessor driven data recorder. The recorder documents the data which can be downloaded onto a laptop or other device. Optionally, the sensor could have a low pass filter to filter out all optical light and only allow detection of UV light. The operator reads the UV irradiance stored in the recorder to validate the installation irradiance.

FIG. 1 illustrates a schematic block diagram of a system 100 for disinfecting a component 102, according to an embodiment of the present disclosure. The component 102 can be any structure that is to be disinfected with UV light. For example, the component 102 can be a structure within a vehicle, a fixed building, or the like. As example, the component 102 can be a passenger seat within a vehicle, a portion of a lavatory (such as a toilet, sink, door handle, and/or the like), a counter or other such surface within a kitchen or galley, and/or the like.

The system 100 includes a UV lamp 104 that includes a plurality of modules 106 coupled together. For example, the UV lamp 104 includes a first module 106 coupled to a second module 106. Optionally, the UV lamp 104 can include more than two modules 106.

Each module 106 includes one or more UV light emitters 108 that are configured to emit UV light through an aperture 112. The UV light emitters 108 can emit UV light within the far UV spectrum, such as between 200 nanometers (nm)-230 nm. For example, the UV light emitters can emit UV light at 222 nm. As another example, the UV light emitters 108 can emit UV light within the UVC spectrum, such as between 230 nm and 280 nm. For example, the UV light emitters can emit UV light at 254 nm. In at least one embodiment, the UV light emitters 108 of the modules 106 emit UV light at the same wavelength. In at least one other embodiment, the UV light emitters 108 of the modules 106 emit UV light at different wavelengths. For example, the UV light emitters 108 of a first module 106 emit UV light within the far UV spectrum, and the UV light emitters 108 of a second module 106 emit UV light within the UVC spectrum, or vice versa.

The modules 106 are coupled together to form the light emitting portion of the UV lamp 104. The modules 106 can be removably coupled together. As such, the UV lamp 104 provides a modular assembly that can be customized to a desired size, shape, and lighting capability. Further, if a module 106 is in need of repair, the module 106 can be removed from the UV lamp 104 and replaced within another module 106. Accordingly, the modules 106 allow for efficient production and maintenance of the UV lamp 104.

In at least one embodiment, portions of the modules 106 are covered with one or more electromagnetic interference (EMI) shields 114. For example, in at least one embodiment, the one or more UV light emitters 108 are surrounded on one or more surfaces with an EMI shield 114, with the aperture 112 being uncovered by the EMI shield 114. In at least one embodiment, the EMI shield 114 is a metal cover, such as a foil formed of aluminum, steel, or the like that covers a housing of the module 106 with the aperture 112 remaining uncovered. Optionally, the modules 106 do not include the EMI shield 114.

The UV lamp 104 can be part of a wand assembly, which is configured to be held by an individual. The wand assembly can be coupled to a backpack assembly, a case assembly, a cart, and/or the like. As another example, the wand assembly can be a standalone assembly that is not coupled to a backpack assembly, a case assembly, a cart, or the like.

As another example, the UV lamp 104 can be a fixture within an area. For example, the UV lamp 104 can be secured within a lavatory, galley, kitchen, or various other areas. The UV lamp 104 can be fixed in position within the area. Optionally, the UV lamp 104 can be movable between a stowed position and a deployed position within the area. In at least one other embodiment, the UV lamp 104 can be removably securable to various structures, such as securing mounts located within an area, such as within a vehicle.

In at least one embodiment, the system 100 also includes an infrared (IR) sensor 116 in communication with a control unit 118, such as through one or more wired or wireless connections. The control unit 118 is also in communication with the UV light emitters 108 of the modules 106, such as through one or more wired or wireless connections. In at least one embodiment, the UV lamp 104 includes the IR sensor 116 and/or the control unit 118. Optionally, the IR sensor 116 and/or the control unit 118 can be remotely located from the UV lamp 104.

In operation, the control unit 118 selectively activates and deactivates the UV light emitters 108 based on an IR signal emitted by and received from the IR sensor 116. For example, the IR sensor 116 is configured to receive an IR light signal 119 emitted by an IR source 120, either directly from the IR source 120, or indirectly from a reflector that receives and reflects the IR light signal 119 from the IR source 120. When the IR sensor 116 receives the IR light signal 119, the IR sensor 116 outputs a sensed IR signal 122 to the control unit 118. Based on the received sensed IR signal 122, the control unit 118 activates the one or more UV light emitters 108 to emit the UV light. If, however, the IR sensors 116 does not receive the IR light signal 119 (such as if the IR light signal 119 is blocked by an individual), the IR sensor does not output the sensed IR signal 122 to the control unit 118. In response to not receiving the sensed IR signal 122, the control unit 118 deactivates the UV light emitters 108 so that they do not emit the UV light.

In at least one embodiment, an activation switch 124 is in communication with the control unit 118, such as through one or more wired or wireless connections. The activation switch 124 can be secured to the UV lamp 104. That is, the UV lamp 104 can include the activation switch 124. Optionally, the activation switch 124 can be remotely located from the UV lamp 104. When the activation switch 124 is engaged to activate the UV light emitters 108, the control unit 118 operates as explained above (that is, the control unit 118 selectively activates and deactivates the UV light emitters based on the signal received from the IR sensor 116). When the activation switch 124 is disengaged so that the UV light emitters 108 are not to emit the UV light, the control unit 118 maintains the UV light emitters 108 in a deactivated state even if the sensed IR signal 122 is received from the IR sensor 116. Optionally, the system 100 may not include the activation switch.

In at least one embodiment, the system 100 includes the UV lamp 104 having UV light emitters 108 whether or not within the modules 106. For example, the UV lamp 104 can be a single, non-modular assembly that is in communication with the control unit 118, which selectively activates and deactivates the UV light emitters 108 as described herein. In at least one other embodiment, the system 100 does not include the IR sensor 116 or the IR source 120.

As used herein, the term "control unit," "central processing unit," "CPU," "computer," or the like may include any processor-based or microprocessor-based system including systems using microcontrollers, reduced instruction set computers (RISC), application specific integrated circuits (ASICs), logic circuits, and any other circuit or processor including hardware, software, or a combination thereof capable of executing the functions described herein. Such are exemplary only, and are thus not intended to limit in any way the definition and/or meaning of such terms. For example, the control unit 118 (and the control unit 618 shown in FIG. 36) may be or include one or more processors that are configured to control operation, as described herein.

The control unit 118 and the control unit 618 are configured to execute a set of instructions that are stored in one or more data storage units or elements (such as one or more memories), in order to process data. For example, the control unit 118 and the control unit 618 may include or be coupled to one or more memories. The data storage units may also store data or other information as desired or needed. The data storage units may be in the form of an information source or a physical memory element within a processing machine.

The set of instructions may include various commands that instruct the control unit 118 and the control unit 618 as a processing machine to perform specific operations such as the methods and processes of the various embodiments of the subject matter described herein. The set of instructions may be in the form of a software program. The software may be in various forms such as system software or application software. Further, the software may be in the form of a collection of separate programs, a program subset within a larger program, or a portion of a program. The software may also include modular programming in the form of object-oriented programming. The processing of input data by the processing machine may be in response to user commands, or in response to results of previous processing, or in response to a request made by another processing machine.

The diagrams of embodiments herein may illustrate one or more control or processing units, such as the control unit 118 and the control unit 618. It is to be understood that the processing or control units may represent circuits, circuitry, or portions thereof that may be implemented as hardware with associated instructions (e.g., software stored on a tangible and non-transitory computer readable storage medium, such as a computer hard drive, ROM, RAM, or the like) that perform the operations described herein. The hardware may include state machine circuitry hardwired to perform the functions described herein. Optionally, the hardware may include electronic circuits that include and/or are connected to one or more logic-based devices, such as microprocessors, processors, controllers, or the like. Optionally, the control unit 118 and the control unit 618 may represent processing circuitry such as one or more of a field programmable gate array (FPGA), application specific integrated circuit (ASIC), microprocessor(s), and/or the like. The circuits in various embodiments may be configured to execute one or more algorithms to perform functions described herein. The one or more algorithms may include aspects of embodiments disclosed herein, whether or not expressly identified in a flowchart or a method.

As used herein, the terms "software" and "firmware" are interchangeable, and include any computer program stored in a data storage unit (for example, one or more memories) for execution by a computer, including RAM memory, ROM memory, EPROM memory, EEPROM memory, and non-volatile RAM (NVRAM) memory. The above data storage unit types are exemplary only, and are thus not limiting as to the types of memory usable for storage of a computer program.

Figure 2:
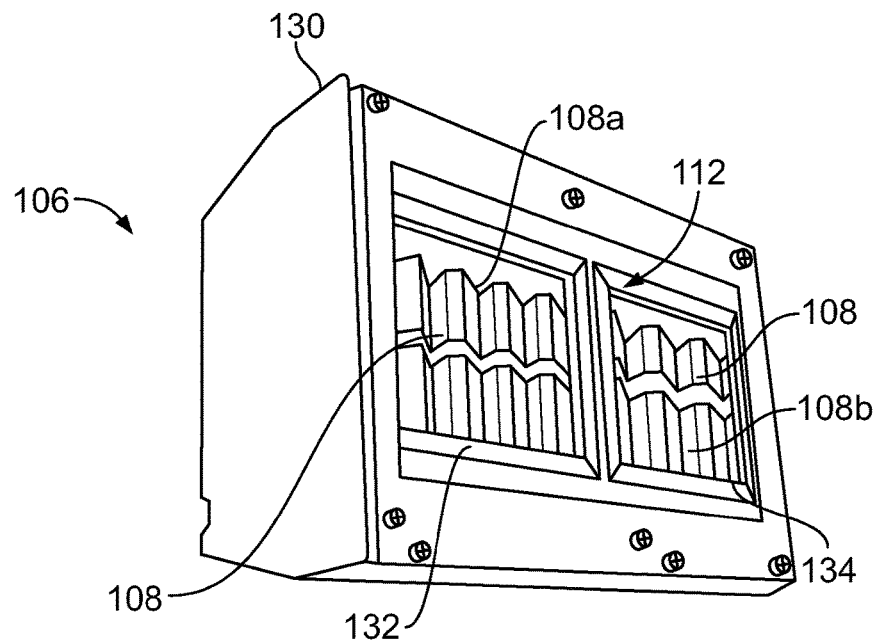
FIG. 2 illustrates a perspective bottom view of a module, according to an embodiment of the present disclosure.

FIG. 2 illustrates a perspective bottom view of a module 106, according to an embodiment of the present disclosure. The module 106 includes a housing 130 that retains a plurality of UV light emitters 108 that are configured to emit UV light through the aperture 112. As shown, the module 106 includes a first plurality of UV light emitters 108*a* and a second plurality of UV light emitters 108*b*. The first plurality of UV light emitters 108*a* are contained within a first sub-housing 132, and the second plurality of UV light emitters 108*b* are contained within a second sub-housing 134 that is distinct from the first sub-housing 132. Each of the first sub-housing 132 and the second sub-housing 134 can contain more or less UV light emitters 108 than shown. Optionally, the module 106 can include a single sub-housing that retains all of the UV light emitters 108 shown in FIG. 2. In at least one embodiment, the module 106 can include a single UV light emitter 108, instead a plurality of UV light emitters 108. In at least one embodiment, the UV light emitters 108*a* and 108*b* can be parallel to a longitudinal axis of the module 106. In at least one other embodiment, the UV light emitters 108*a* and 108*b* can be perpendicular to the longitudinal axis of the module 106. In at least one other embodiment, the UV light emitters 108*a* and 108*b* can be other than parallel or perpendicular to the longitudinal axis of the module 106.

Figure 3:
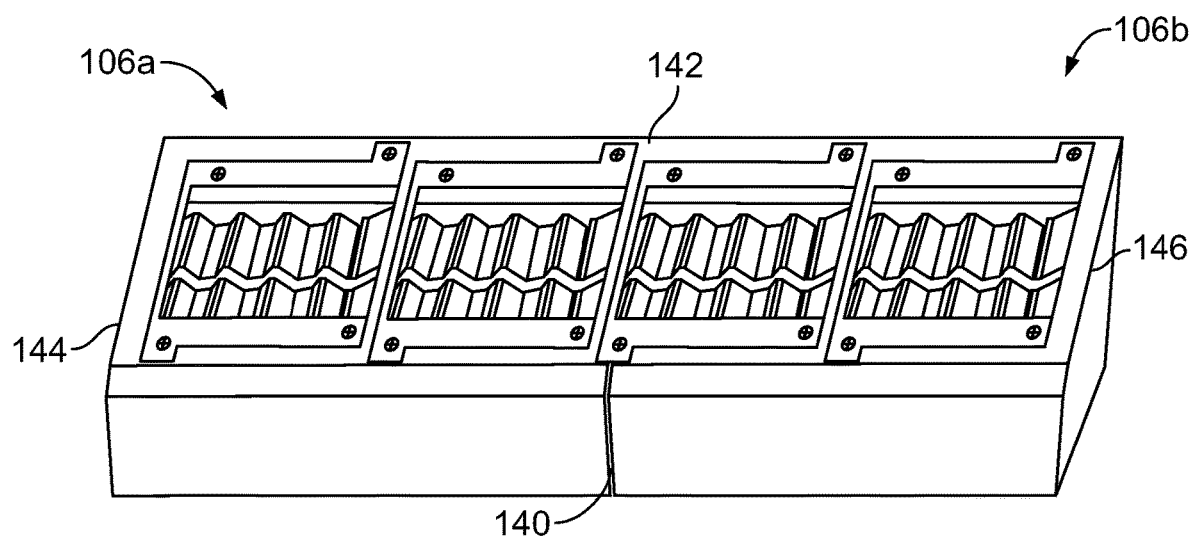
FIG. 3 illustrates a perspective bottom view of a first module coupled to a second module, according to an embodiment of the present disclosure.

FIG. 3 illustrates a perspective bottom view of a first module 106*a* coupled to a second module 106*b*, according to an embodiment of the present disclosure. A first end 140 of the first module 106*a* is coupled to an opposite second end 142 of the second module 106*b*. Optionally, the first module 106*a* and the second module 106*b* can be coupled together in a side-to-side fashion. Another module (not shown in FIG. 3) can be coupled to a second end 144 of the first module 106*a*. Further, another module (not shown in FIG. 3) can be coupled to a first end 146 of the second module 106*b*.

The modules 106*a* and 106*b*, as well as additional modules, can be stacked end-to-end, and/or side-to-side, as desired, to provide various illumination patterns. The first module 106*a* and the second module 106*b* can be removably coupled together, such as through one or more fasteners, bonding, a dove tail joint, a lap joint, a plug and socket connection, and/or the like. As such, the first module 106*a* and the second module 106*b* can be efficiently coupled together. Further, the first module 106*a* and the second module 106*b* can be disconnected, such as if one of the first module 106 or the second module 106*b* is in need of repair or is to be replaced.

Figure 4:
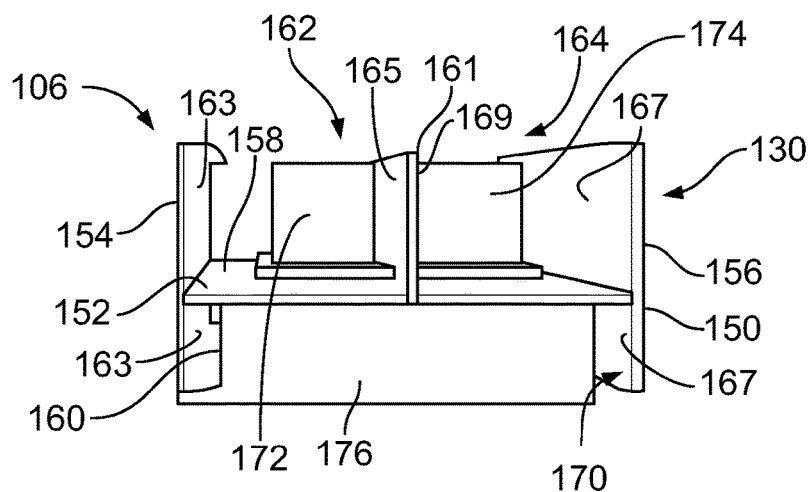
FIG. 4 illustrates a perspective end view of a module, according to embodiment of the present disclosure.
Figure 5:
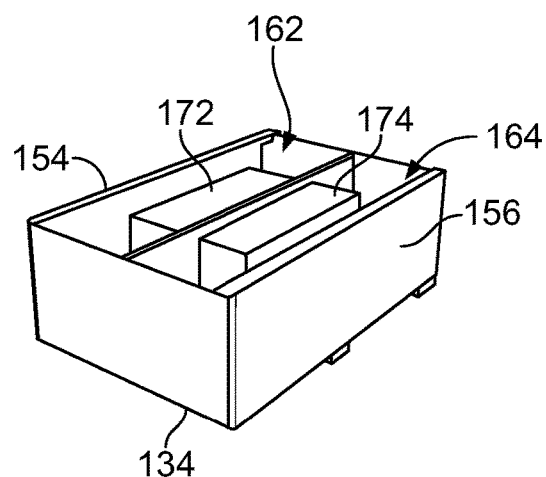
FIG. 5 illustrates a perspective top view of the module of FIG. 4.
Figure 6:
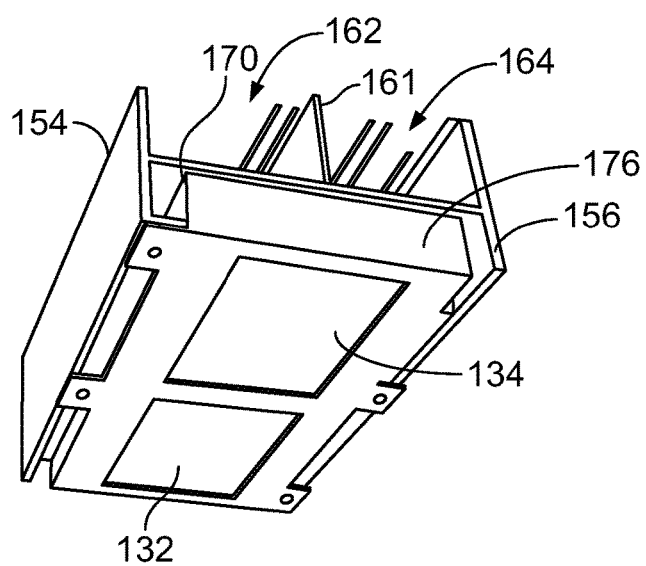
FIG. 6 illustrates a perspective bottom view of the module of FIG. 4.

FIG. 4 illustrates a perspective end view of a module 106, according to embodiment of the present disclosure. FIG. 5 illustrates a perspective top view of the module 106 of FIG. 4. FIG. 6 illustrates a perspective bottom view of the module 106 of FIG. 4. Referring to FIGS. 4-6, for the sake of clarity, certain outer wall portions of the module 106 are not shown in order show internal components.

In at least one embodiment, the housing 130 includes a bracket 150 having a platform 152 extending between opposite side walls 154 and 156. The platform 152 includes an upper surface 158 opposite from a lower surface 160. A dividing wall 161 upwardly extends from the upper surface 156. A first power chamber 162 is defined between the upper surface 158, an interior surface 163 of the side wall 154, and a first side surface 165 of the dividing wall 161. A second power chamber 164 is defined between the upper surface 158, an interior surface 167 of the side wall 156, and a second side surface 169 (opposite from the first side surface 165) of the dividing wall 161. An emitter chamber 170 is defined between the lower surface 158, the interior surface 163 of the side wall 154, and the interior surface 167 of the side wall 156.

A first power supply 172 is secured within the first power chamber 162. A second power supply 174 is secured within the second power chamber 164. Referring to FIGS. 1-6, the first power supply 172 and the second power supply 174 may be batteries and/or electrical power interfaces, connections, and/or the like that are configured to provide power to the UV light emitters 108.

In at least one embodiment, a frame 176 is secured within the emitter chamber 170, such as via one or more fasteners, bonding, and/or the like. The frame 176 retains the first sub-housing 132 and the second sub-housing 134. The UV light emitters 108 of the first sub-housing 132 and the second sub-housing 134 are electrically coupled to the first power supply 172 and the second power supply 174, respectively, such as through wires that pass through slots, channels, or other such openings formed in the platform 152.

The platform 152 separates and isolates the frame 176 (including the UV light emitters 108) from the first power supply 172 and the second power supply 174. Further, the dividing wall 161 separates and isolates first power supply 172 from the second power supply 174. In at least one embodiment, the first power supply 172 and the second power supply 174 can be high voltage power supplies (such as 2 kV), and therefore the separation and isolation therebetween and in relation to the frame 176 ensures reliable and efficient operation.

As shown, the first power supply 172 and the second power supply 174 are stacked above the frame 176, which retains the first sub-housing 132 and the second sub-housing 134. Optionally, a single power supply can be used to provide power to the UV light emitters 108 of the first sub-housing 132 and the second sub-housing 134. In at least one embodiment, the bracket 150 may not include the dividing wall 161. In at least one other embodiment, the power suppl(ies) can be remote from the module 106.

Figure 7:
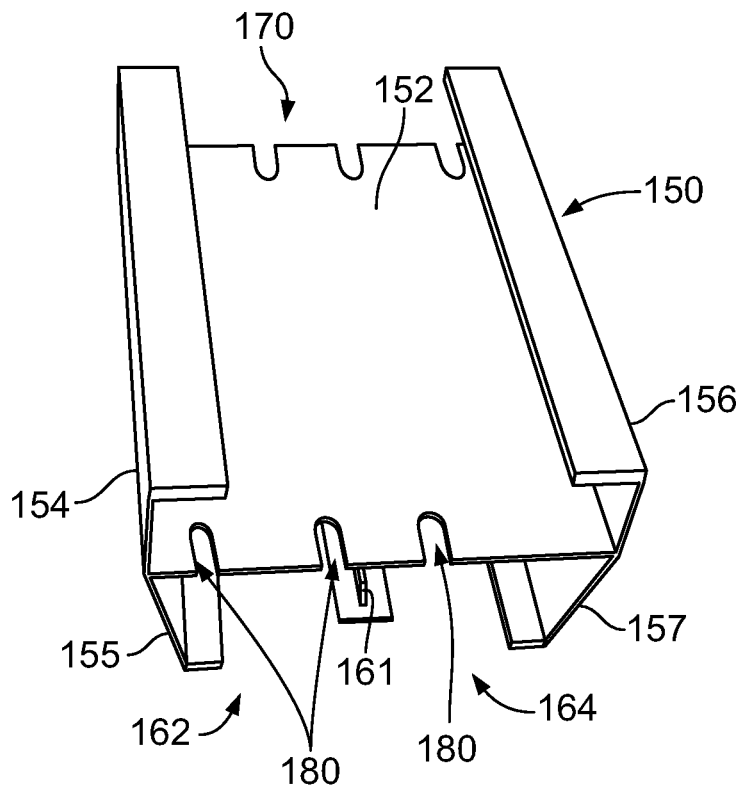
FIG. 7 illustrates a perspective bottom view of a bracket, according to an embodiment of the present disclosure.
Figure 8:
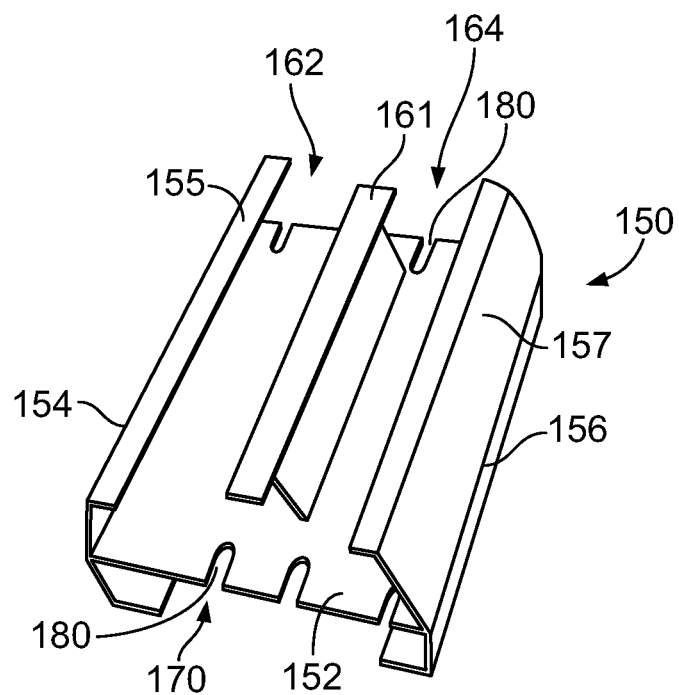
FIG. 8 illustrates a perspective top view of the bracket of FIG. 7.

FIG. 7 illustrates a perspective bottom view of the bracket 150, according to an embodiment of the present disclosure. FIG. 8 illustrates a perspective top view of the bracket 150 of FIG. 7. Referring to FIGS. 7 and 8, the bracket 150 can include one or more passages 180 (such as slots) formed through the platform 152. Referring to FIGS. 1-8, the passages 180 allow for wiring to be routed between the UV light emitters 108 and the power supplies 172 and/or 174, for example. Optionally, the bracket 150 may not include the passages 180. Instead, wiring can be routed around end edges of the platform 152, for example.

As shown, the side walls 154 and 156 can includes inwardly-canted segments 155 and 157, respectively, bounding the first power chamber 162 and the second power chamber 164, respectively. Free ends of the inwardly-canted segments angle toward the dividing wall 161. The inwardly-canted segments 155 and 157 provide a more compact bracket 150, which takes up less space. Optionally, the side walls 154 and 156 can also, or alternatively, include inwardly-canted segments. Alternatively, the bracket 150 may not include inwardly-canted segments.

Figure 9:
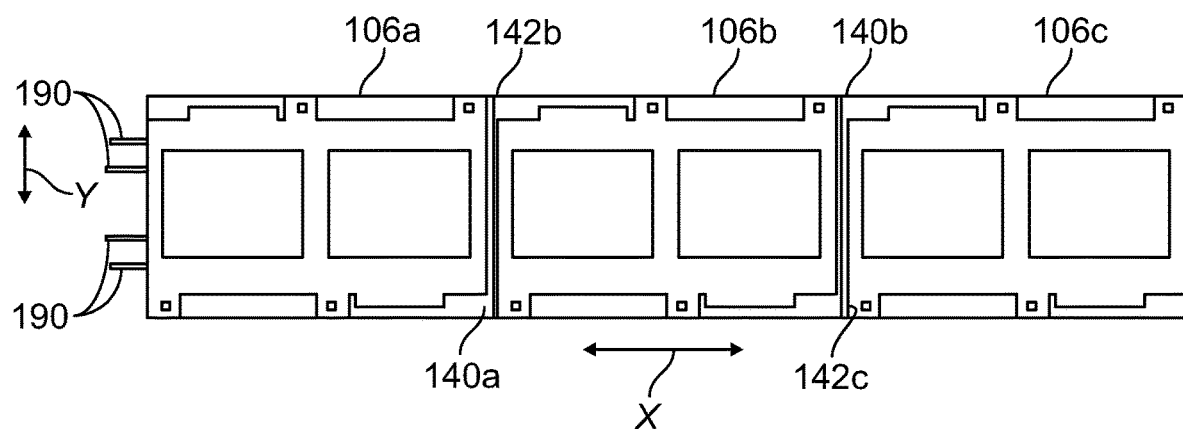
FIG. 9 illustrates a bottom view of a plurality of modules coupled together, according to an embodiment of the present disclosure.

FIG. 9 illustrates a bottom view of a plurality of modules 106a, 106b, and 106c coupled together, according to an embodiment of the present disclosure. A first end 140a of the module 106a is secured to a second end 142b of the module 106b. A first end 140b of the module 106b is secured to a second end 142c of the module 106c. As shown, the modules 106a, 106b, and 106c are linearly aligned in the X direction in an end-to-end configuration. Optionally, one or more of the modules 106a, 106b, and 106c can be aligned in the Y direction a side-to-side configuration. Wiring 190 is routed to each of the modules 106a, 106b, and 106c.

Figure 10:
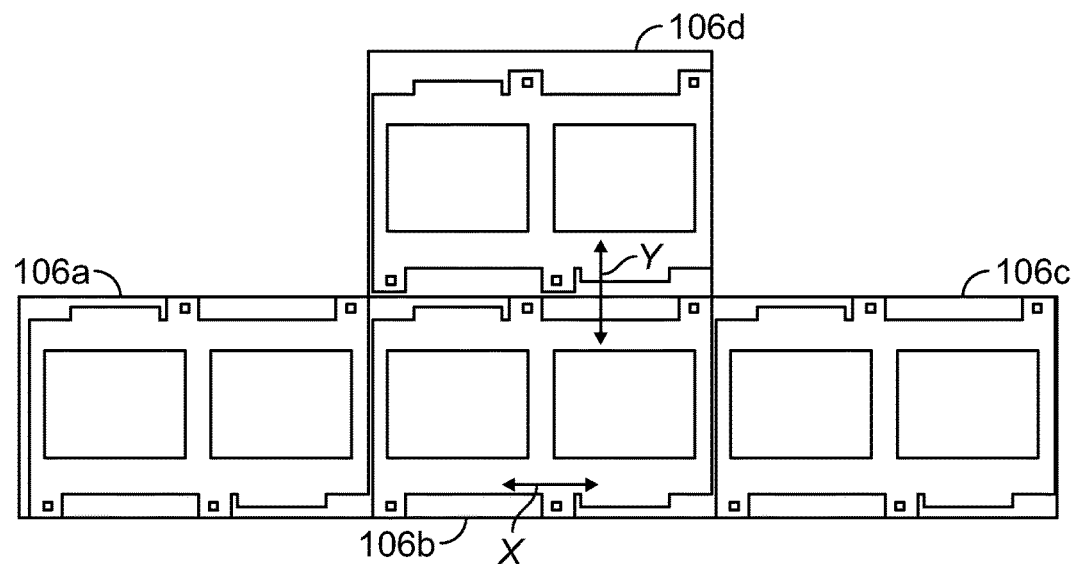
FIG. 10 illustrates a bottom view of a plurality of modules coupled together, according to an embodiment of the present disclosure.

FIG. 10 illustrates a bottom view of a plurality of modules 106a, 106b, 106c, and 106d coupled together, according to an embodiment of the present disclosure. As shown, the module 106d can be secured to the module 106b in a side-to-side fashion. Optionally, the module 106d can be coupled to the module 106a or 106c. In at least one other embodiment, additional modules (not shown) can be coupled to each of the modules 106a, 106b, or 106c in a side-to-side configuration.

Figure 11:
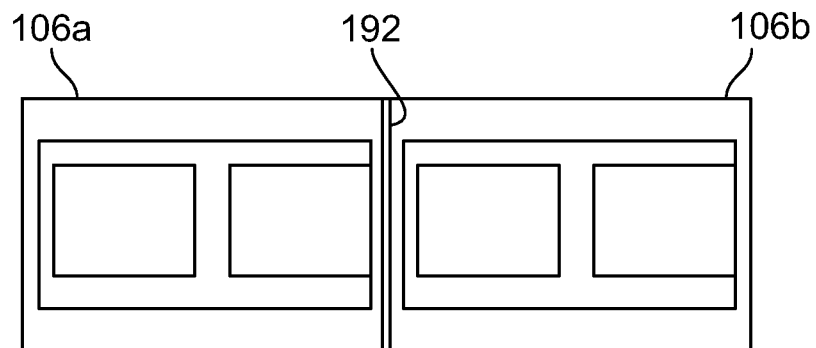
FIG. 11 illustrates a bottom view of a first module coupled to a second module, according to an embodiment of the present disclosure.

FIG. 11 illustrates a bottom view of a first module 106a coupled to a second module 106b, according to an embodiment of the present disclosure. The first module 106a couples to the second module 106b via bonding at a bond interface 192 therebetween.

Figure 12:
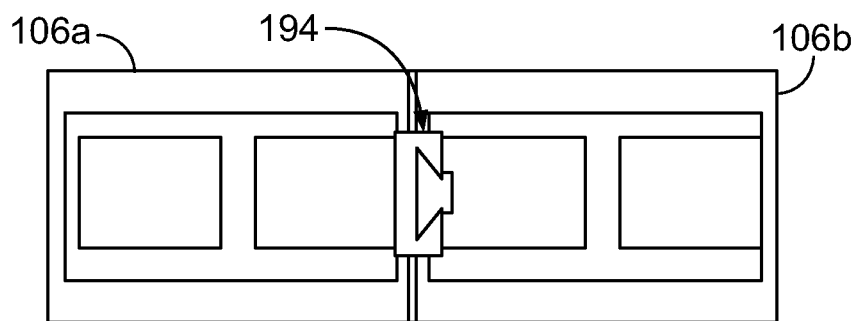
FIG. 12 illustrates a bottom view of a first module coupled to a second module, according to an embodiment of the present disclosure.

FIG. 12 illustrates a bottom view of a first module 106a coupled to a second module 106b, according to an embodiment of the present disclosure. The first module 106a couples to the second module 106b via a connecting joint 194, such as a dove tail joint.

Figure 13:
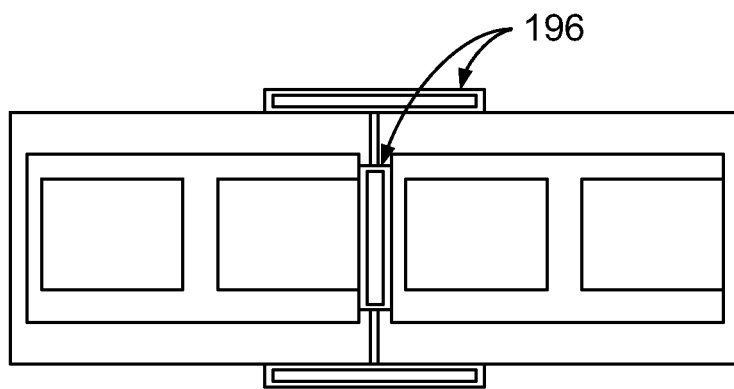
FIG. 13 illustrates a bottom view of a first module coupled to a second module, according to an embodiment of the present disclosure.

FIG. 13 illustrates a bottom view of a first module 106a coupled to a second module 106b, according to an embodiment of the present disclosure. The first module 106a couples to the second module 106b via one or more connecting joints 196, such as lap toil joints at connected ends and/or sides. Fasteners, such as screws or bolts, and/or bonding can be used to secure the connecting joints 196 to the first module 106a and the second module 106b.

Figure 14:
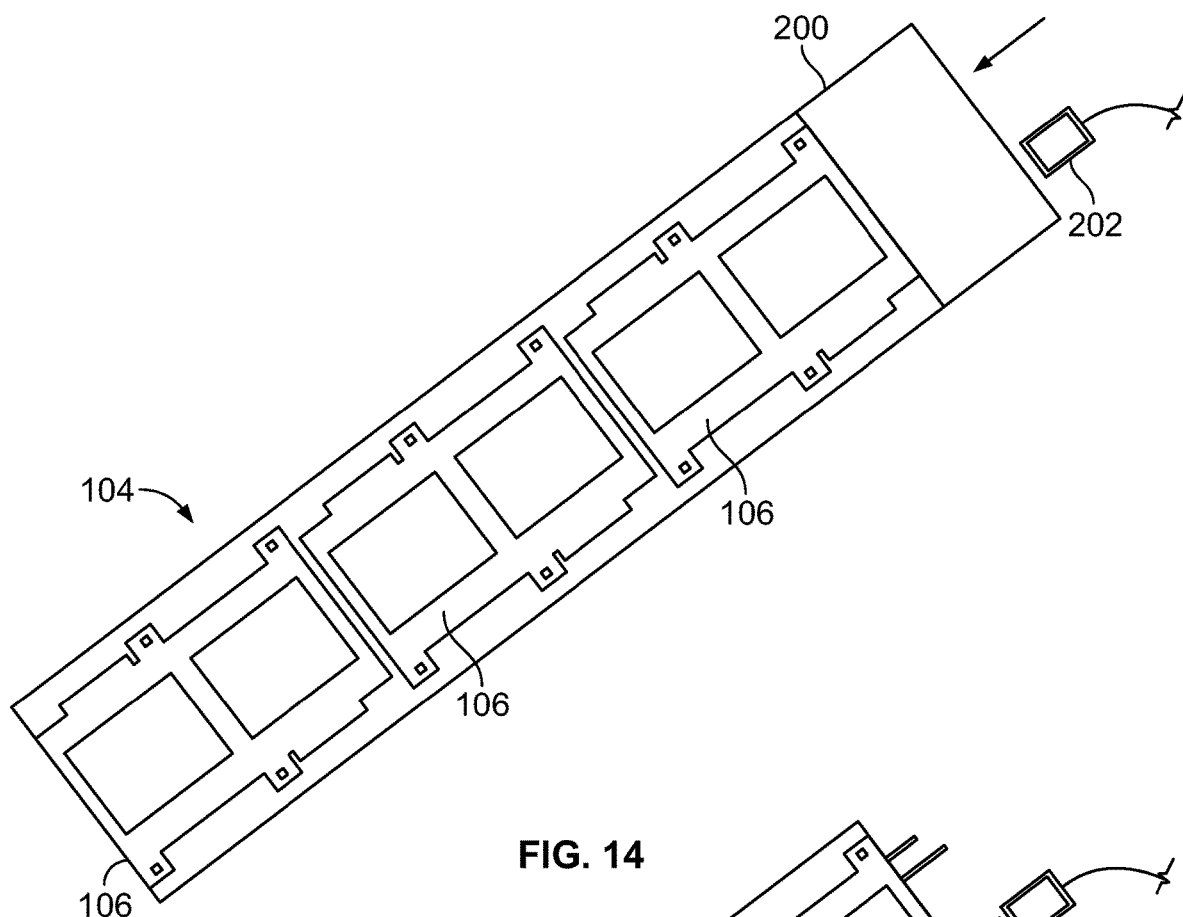
FIG. 14 illustrates a bottom view of a UV lamp having a plurality of modules, according to an embodiment of the present disclosure.

FIG. 14 illustrates a bottom view of the UV lamp 104 having a plurality of modules 106, according to an embodiment of the present disclosure. The UV lamp 104 can include a battery 200, such as 24 V battery, that provides power to the power supplies of the modules 106. In at least one embodiment, the battery 200 is configured to mate with a power cord 202 to be recharged.

Figure 15:
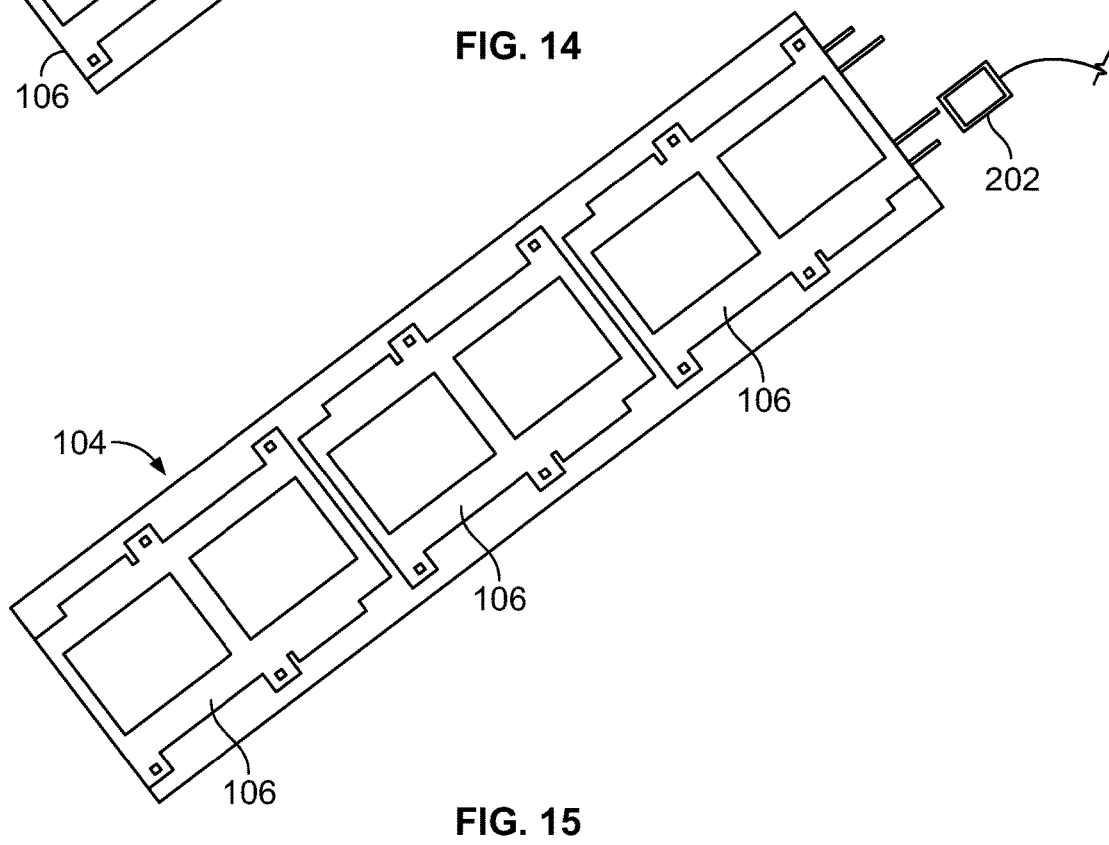
FIG. 15 illustrates a bottom view of a UV lamp having a plurality of modules, according to an embodiment of the present disclosure.

FIG. 15 illustrates a bottom view of the UV lamp 104 having a plurality of modules 106, according to an embodiment of the present disclosure. In this embodiment, the UV lamp 104 may not include a battery. Instead, the UV lamp receives power from the power cord 202.

Figure 16:
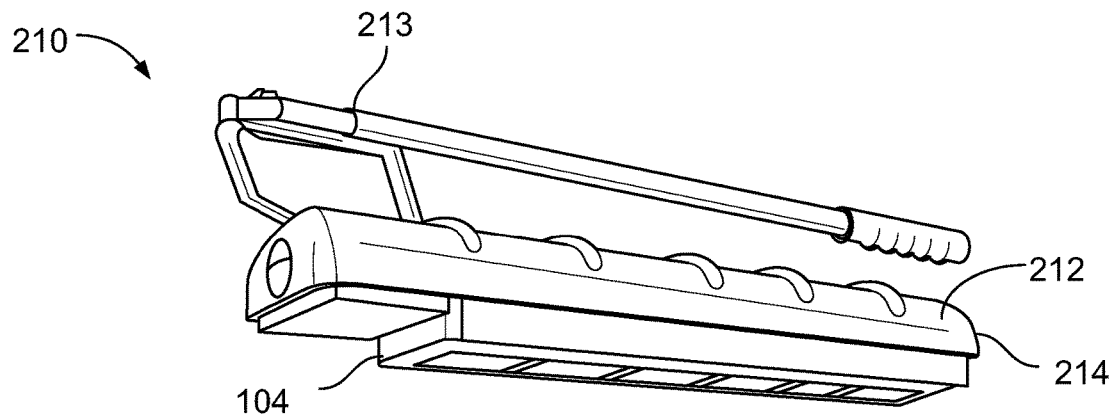
FIG. 16 illustrates a perspective lateral view of a wand assembly including a UV lamp, according to an embodiment of the present disclosure.
Figure 17:
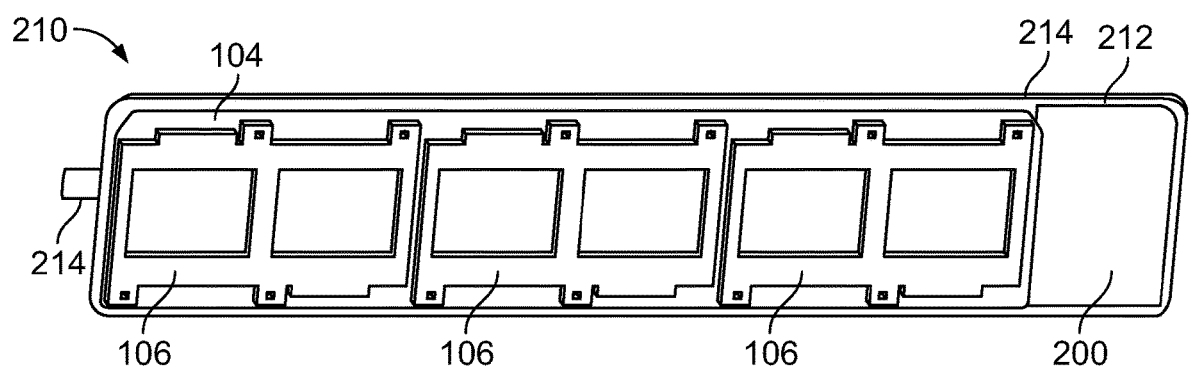
FIG. 17 illustrates a bottom view of the wand assembly of FIG. 16.

FIG. 16 illustrates a perspective lateral view of a wand assembly 210 including the UV lamp 104, according to an embodiment of the present disclosure. FIG. 17 illustrates a bottom view of the wand assembly of FIG. 16. Referring to FIGS. 16 and 17, the wand assembly 210 includes a sanitizing head 212 coupled to a handle 213. The sanitizing head 212 includes a shroud 214 that retains the UV lamp 104. The battery 200 can be retained within the shroud 214.

In at least one embodiment, the sanitizing head 212 is configured to move relative to the handle 213. For example, the sanitizing head 212 can be extended and/or rotated relative to the handle 213. In at least one other embodiment, the sanitizing head 212 is fixed in relation to the handle 213. The wand assembly 210 can include the UV lamp 104 having a plurality of modules 106, as described with respect to any of FIGS. 1-15.

Figure 18:
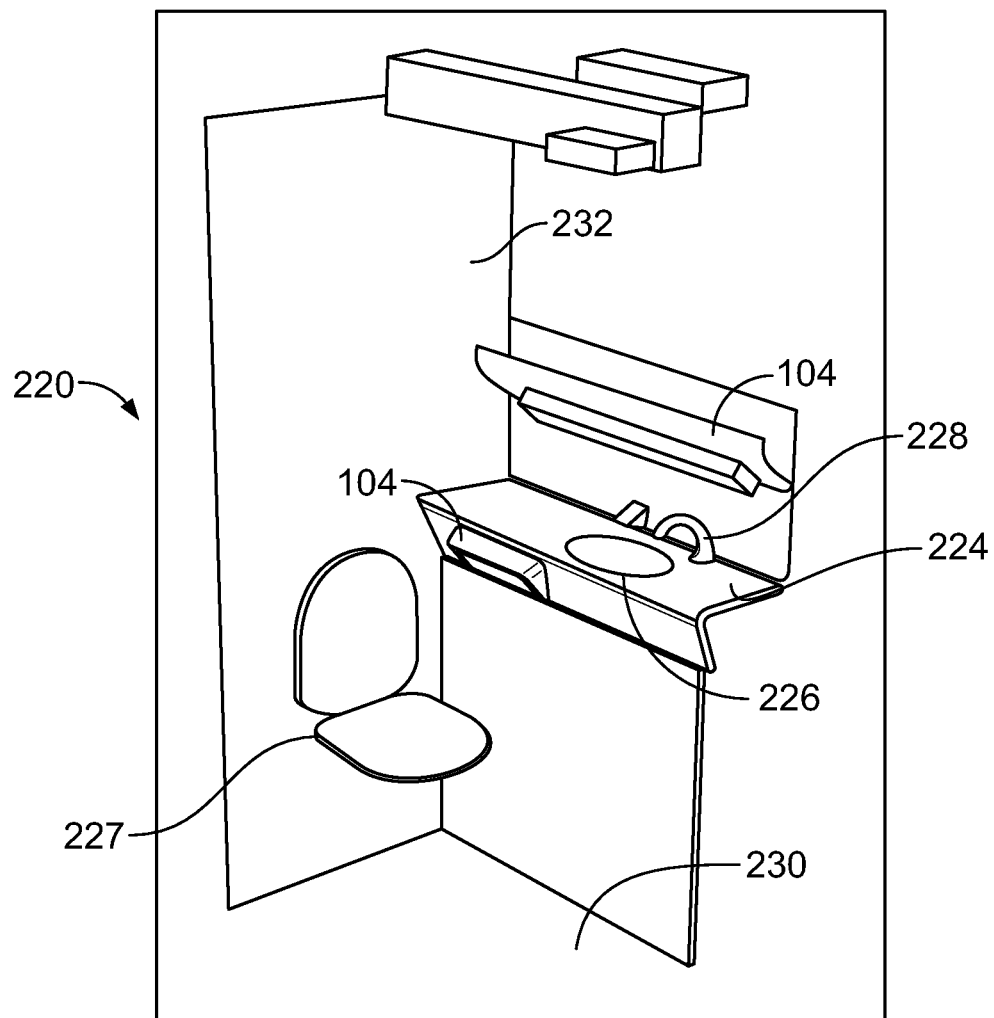
FIG. 18 illustrates a perspective internal view of a lavatory, according to an embodiment of the present disclosure.

FIG. 18 illustrates a perspective internal view of a lavatory 220, according to an embodiment of the present disclosure. The lavatory 220 may be within an internal cabin of a vehicle, such as a commercial aircraft. The lavatory 220 includes a toilet 222 and a counter 224 having a sink 226 and faucet 228. One or more UV lamps 104 are disposed within the lavatory 220. The UV lamps 104 are configured as described with respect to any of FIGS. 1-15.

The UV lamps 104 are configured to emit UV light to disinfect one or more components within the lavatory 220, such as the toilet 222, the counter 224, the sink 226, the faucet 228, the floor 230, one or more walls 232, and/or the like. In at least one embodiment, the UV lamps 104 can be fixed in position. In at least one other embodiment, the UV lamps 104 can be configured to move. For example, the UV lamps 104 can be moved between stowed positions and deployed positions.

Figure 19:
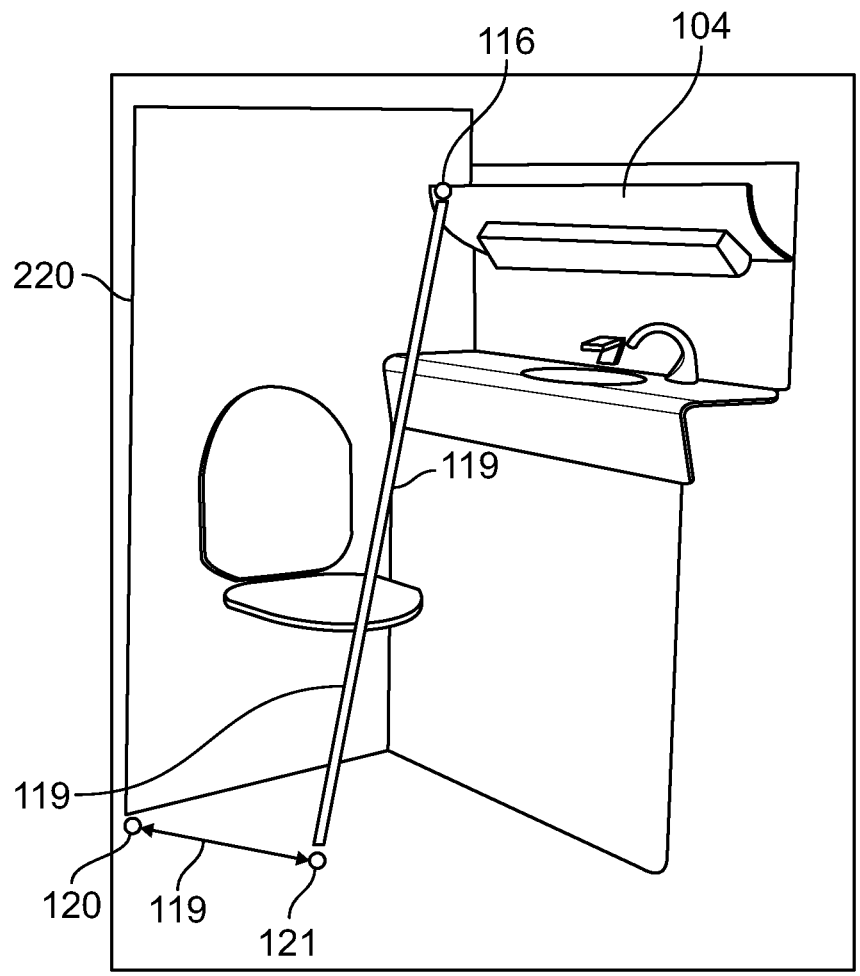
FIG. 19 illustrates a perspective internal view of the lavatory, according to an embodiment of the present disclosure.

FIG. 19 illustrates a perspective internal view of the lavatory 220, according to an embodiment of the present disclosure. Referring to FIGS. 1 and 19, in this embodiment, the UV lamp 104 includes the IR sensor 116 that receives the IR light signal 119 from the IR source 120. The IR source 120 is configured to emit the IR light signal 119 through an area in which an individual would be if occupying the lavatory 220.

The IR sensor 116 may be aligned with the IR source 120 to directly receive the IR light signal 119 from the IR source 120. Optionally, the IR source 120 may be configured to emit the IR light signal 119 at a reflector, such as a mirror, that reflect the IR light signal 119 to the IR source 120.

The IR sensor 116 can be mounted directly to the UV lamp 104, such as on a housing. In at least one embodiment, the IR sensor 116 can be secured to a module 106. In at least one embodiment, multiple modules 106 include an IR sensor 116. In at least one other embodiment, the IR sensor 116 is remote from the UV lamp 104.

As shown, the IR sensor 116 can be secured to an end or corner of the UV lamp 104. The IR sensor 116 is configured to receive the IR light signal 119 either directly from the IR source 120 or indirectly from the IR source 120 as reflected from one or more reflectors 121. The IR light signal 119 can be a laser or narrow non-laser optical signal, for example.

As shown, the IR light signal 119 is configured to extend through a portion of the lavatory 220 such that a person entering or exiting the room crosses the path of and interrupts the IR light signal 119. As the path between the IR source 120 and the IR sensor 116 is interrupted, the IR sensor 116 does not receive the IR light signal 119. When the IR sensor 116 does not receive the IR light signal 119, the control unit 118 does not receive the sensed IR signal 122 from the IR sensor 116. Further, the IR light signal 119 is directed such that an individual within the lavatory 220 would interrupt the IR light signal 119.

Figure 23:
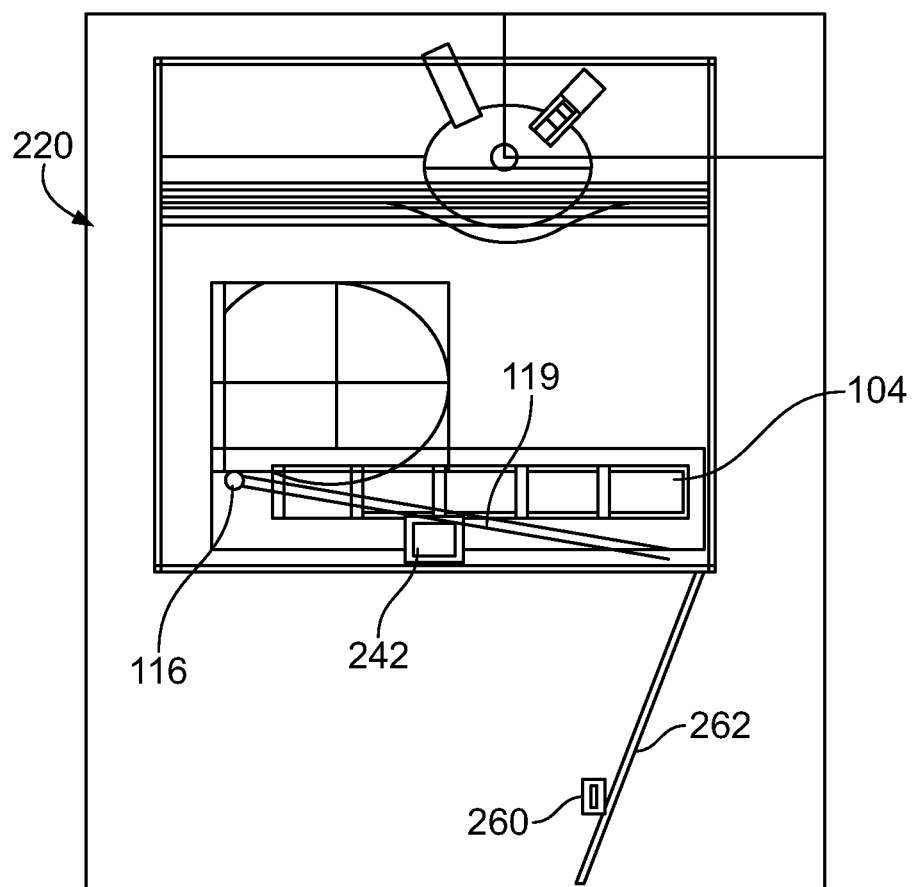
FIG. 23 illustrates a top plan view of a lavatory, according to an embodiment of the present disclosure.
Figure 24:
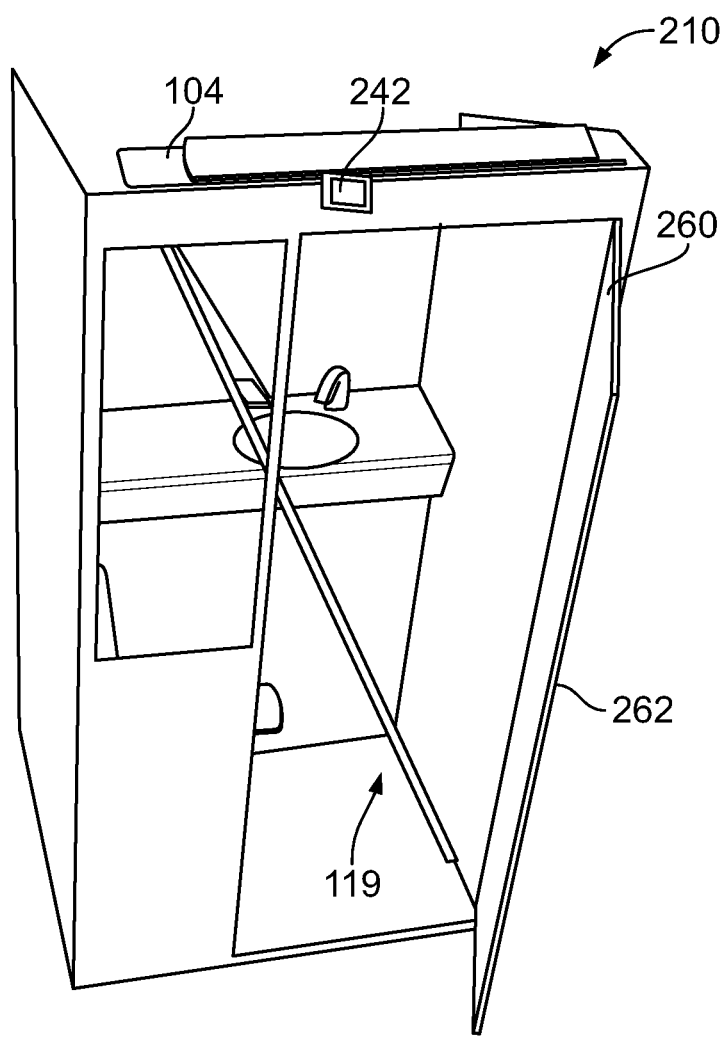
FIG. 24 illustrates a perspective internal view of the lavatory of FIG. 23.

The control unit 118 operates to ensure that the UV light emitters 108 are deactivated when an individual is within the lavatory 220 (or other such room in which the UV lamp 104 is used). By communicating with the IR sensor 116 (and optionally, the door sensor 242 as shown in FIGS. 23 and 24), the control unit 118 determines whether the room is occupied or unoccupied. If occupied, the control unit 118 deactivates the UV light emitters 108. If unoccupied, the control unit 118 can activate the UV light emitters 108 to disinfect one or more components within the room.

Figure 20:
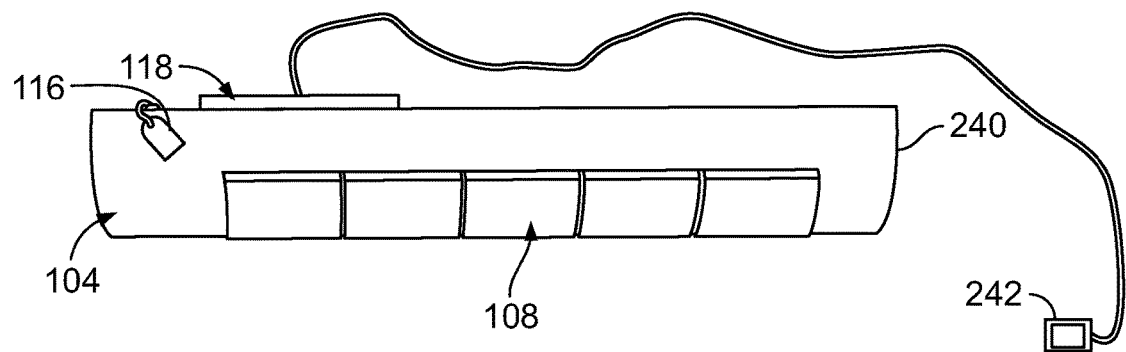
FIG. 20 illustrates a perspective bottom view of a UV lamp, according to an embodiment of the present disclosure.

FIG. 20 illustrates a perspective bottom view of the UV lamp 104, according to an embodiment of the present disclosure. Referring to FIGS. 1 and 2, the UV lamp 104 104 includes a housing 240 having a plurality of UV light emitters 108, whether within modules 106 or not. The IR sensor 116 is secured to the housing 240 and is oriented in a direction to receive the IR light signal 119.

The control unit 118 is in communication with the IR sensor 116 and the UV light emitters 108. In at least one embodiment, a door sensor 242 is also in communication with the control unit 118, such as through one or more wired or wireless connections. For example, the door sensor 242 is a Hall-effect sensor. The door sensor 242 is configured to detect opening and closing of a door of a room, such as the lavatory 220 shown in FIGS. 18 and 19. The control unit 118 selectively activates and deactivates the UV light emitters 108 based on IR signals (for example reception of such IR signal(s) and lack of reception of such IR signal(s) received from the IR sensor 116 and door signals (for example, signals indicating that the door is open or closed) received from the door sensor 242. Optionally, the control unit 118 is not in communication with a door sensor.

Figure 21:
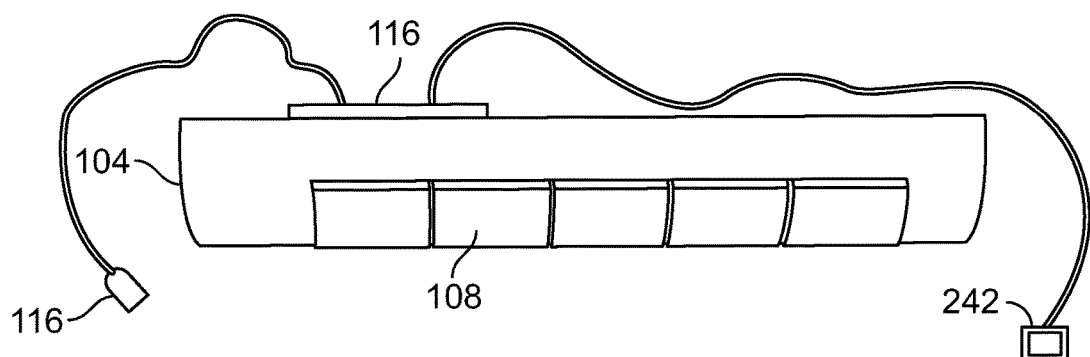
FIG. 21 illustrates a perspective bottom view of a UV lamp, according to an embodiment of the present disclosure.

FIG. 21 illustrates a perspective bottom view of the UV lamp 104, according to an embodiment of the present disclosure. In this embodiment, the IR sensor 116 is remotely located from the UV lamp 104, and is in communication with the control unit 118 through one or more wired or wireless connections.

Figure 22:
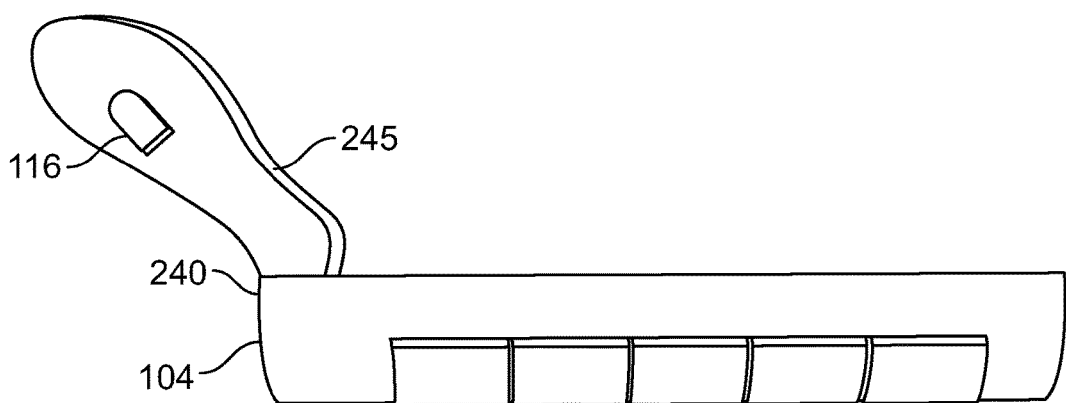
FIG. 22 illustrates a perspective bottom view of a UV lamp, according to an embodiment of the present disclosure.

FIG. 22 illustrates a perspective bottom view of the UV lamp 104, according to an embodiment of the present disclosure. As shown, the housing 240 can include an extension 245. The IR sensor 116 can be mounted on the extension 245.

FIG. 23 illustrates a top plan view of the lavatory 220, according to an embodiment of the present disclosure. FIG. 24 illustrates a perspective internal view of the lavatory 220 of FIG. 23. Referring to FIGS. 1 and 19-24, the door sensor 242, such as a Hall effect sensor, is configured to cooperate with a magnet 260 positioned on the door 262 of the lavatory 220 to determine when the door 262 is opened or closed. For example, when the magnet 260 touches or is in close proximity (such as within 6 inches or less) of the door sensor 242, the door sensor 242 outputs a signal to the control unit 118 that the door 262 is closed. In at least one embodiment, the door sensor 242 can be secured to the housing 240 of the UV lamp 104.

In at least one embodiment, the control unit 118 deactivates the UV light emitters 108 of the UV lamp 104 in response to the IR sensor 116 not receiving the sensed IR signal 122 from the IR sensor 116. Conversely, the control unit 118 activates the UV light emitters 108 to disinfect one or more components within the lavatory 220 in response to receiving the sensed IR signal 122 from the IR sensor 116 and receiving a signal from the door sensor 242 indicating that the door 262 is closed. In at least one embodiment, in response to receiving a signal from the door sensor 242 indicating that the door 262 is opened, the control unit 118 deactivates the UV light emitters 108, even if the control unit 118 receives the sensed IR signal 122 from the IR sensor 116.

Figure 25:
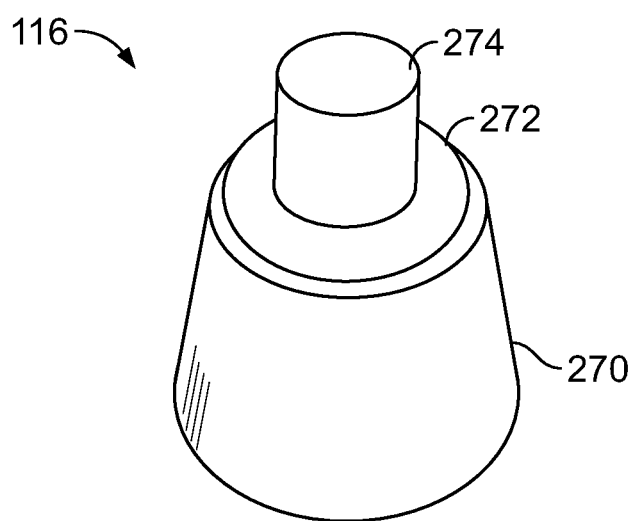
FIG. 25 illustrates a perspective view of an infrared sensor, according to an embodiment of the present disclosure.

FIG. 25 illustrates a perspective view of the IR sensor 116, according to an embodiment of the present disclosure. In at least one embodiment, the IR sensor 116 includes a socket 270 that moveably retains a ball 272. The ball 272 retains a sensing element 274 that is configured to receive and detect an IR light signal. The ball and socket configuration shown in FIG. 25 allows the sensing element 274 to be moved to a desired orientation and alignment so as to receive the IR light signal. Optionally, the IR sensor 116 may not include a movable element, such as the ball 272 moveably retained within the socket 270.

Referring to FIGS. 1 and 19-25, in at least one embodiment, the control unit 118 activates the UV light emitters 108 in response to determining that the lavatory 220 (or other such room) is vacated and unoccupied. For example, in response to reception of a signal from the door sensor 242 that the door 262 is opened and the sensed IR light signal 122 for at least one second, followed by reception of a signal from the door sensor 242 that the door 262 is closed and the sensed IR light signal 122 for at least one additional second, the control unit 118 activates the UV light emitters 108 for a predetermined sanitizing period (such as 5 seconds). If the control unit 118 detects that the door 262 is opened during the sanitizing period, the control unit 118 immediately deactivates the UV light emitters 108.

Further, if the control unit 118 detects that IR sensor 116 is not receiving the IR light signal 119 (such as by not receiving the sensed IR light signal 122 from the IR sensor), the control unit 118 deactivates the UV light emitters 108. Such an interruption of the IR light signal 119 triggers a reset event, in which the control unit 118 may then reactivate the UV light emitters 108 after determining that the door 262 has been opened, reception of the sensed IR light signal 122 from the IR sensor 116, the door 262 is subsequently closed, and further reception of the sensed IR light signal 122 from the IR sensor 116.

Figure 26:
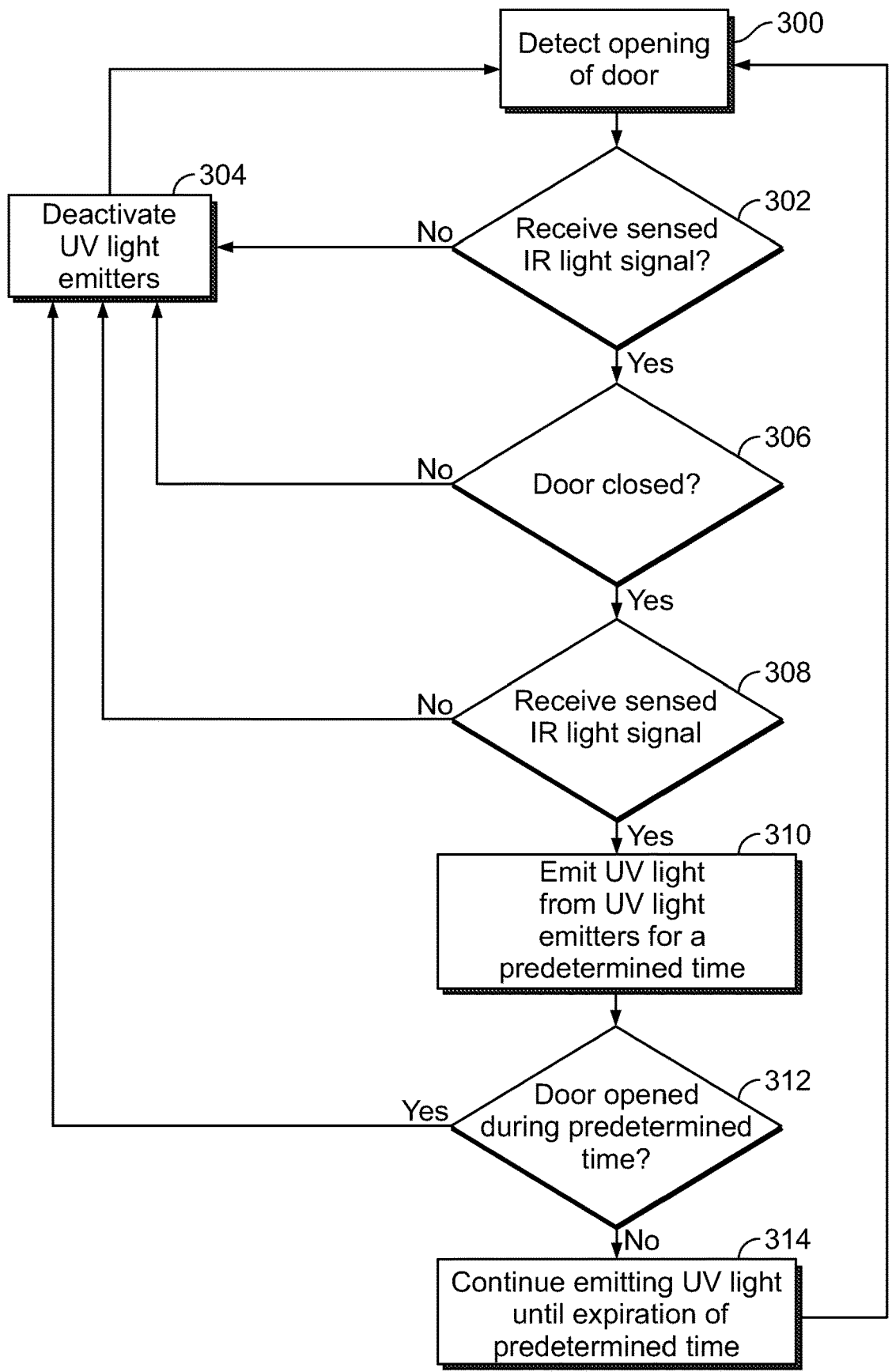
FIG. 26 illustrates a flow chart of a method of operating a UV lamp, according to an embodiment of the present disclosure.

FIG. 26 illustrates a flow chart of a method of operating a UV lamp, according to an embodiment of the present disclosure. Referring to FIGS. 1 and 19-26, at 300, the control unit 118 determines an opening of the door 262, such as via a signal received from the door sensor 242. At 302, the control unit 118 determines if the sensed IR light signal 122 is received from the IR sensor 116. If not, the method proceed to 304, at which the control unit 118 deactivates the UV light emitters 108, and the method then returns to 300.

If, however, the sensed IR light signal 122 is received from the IR sensor 116 at 302, the control unit 118 determines if the door 262 is closed, such as via a signal received from the door sensor 242. If the door is not closed, the method returns to 304.

If, however, the door 262 is closed, the control unit 118 determines if the sensed IR light signal 122 is received at 308. If not, the method returns to 304.

If, however, the control unit 118 determines that the sensed IR light signal 122 is received at 308, the control unit 118 operates the UV lamp 104 at 310 to emit the UV light from the UV light emitters 108 for a predetermined sanitizing time (such as 3-5 seconds). If, at 312, the control unit 118 determines that the door 262 is opened during the predetermined sanitizing time, the method returns to 304, at which the control unit 118 immediately deactivates the UV light emitters 304.

If, however, the door is not opened during the predetermined sanitizing time at 312, the method proceeds from 312 to 314, at which the control unit 118 operates the UV light emitters 108 to continue to emit the UV light until an expiration of the predetermined time, at which point the UV light emitters 108 are deactivated. The process then returns to 300.

Figure 27:
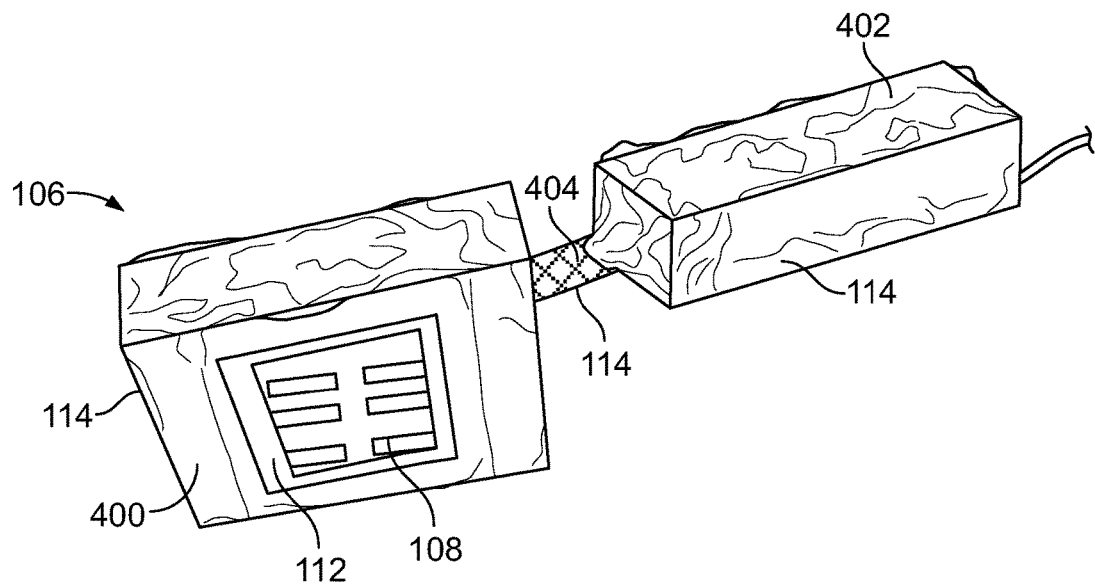
FIG. 27 illustrates a perspective view of a module, according to an embodiment of the present disclosure.

FIG. 27 illustrates a perspective view of a module 106, according to an embodiment of the present disclosure. The module 106 includes a sub-housing 400 retaining one or more UV light emitters 108. The sub-housing 400 is coupled to a power supply 402 through a cable 404. In contrast to the embodiments shown in FIGS. 4-6, the sub-housing 400 and the power supply 402 may not be secured within a common bracket. Optionally, the sub-housing 400 and the power supply 402 may be secured to a bracket, such as the bracket 150 shown and described with respect to FIGS. 4-6, for example.

An EMI shield 114 (for example, a first EMI shield) is disposed around portions of the sub-housing 400. In at least one embodiment, the EMI shield 114 is disposed around all portions of the sub-housing 400, except the aperture 112. As an example, the EMI shield 114 is a metal foil (for example, a stainless steel, aluminum, or the like foil) that extends around portions of the sub-housing 400. The EMI shield 114 blocks, attenuates, or otherwise hinders EMI that may be generated by operation of the UV light emitters 108 from passing therethrough (and/or blocks EMI from passing into the sub-housing 400).

The EMI shield 114 (for example, a second EMI shield) may also extend around portions of the power supply 402 and/or the cable 404. For example, the EMI shield 114 may wrap around all portions of the power supply 402 and/or the cable 404. In at least one embodiment, the EMI shield 114 covers an entirety of the module 106 including the sub-housing 400, the power supply 402, and the cable 404, except for the aperture 112. The EMI shield 114 blocks, attenuates, or otherwise hinders EMI from passing between the sub-housing 400 and the power supply 402.

Further, by separating the sub-housing 400 from the power supply 402 (and connecting via the cable 404), the module 106 may be more readily integrated and used in certain confined areas in which a common housing retaining both may be too large. The sub-housing 400 as shown in FIG. 27 has a low profile and may fit into smaller spaces.

The EMI shield 114 may be used with any of the embodiments described herein. Further, a module including the sub-housing 400 separated from the power supply 402 (as shown in FIG. 27) may be used with any of the embodiments described herein, whether with the EMI shield 114 or without the EMI shield 114.

Figure 28:
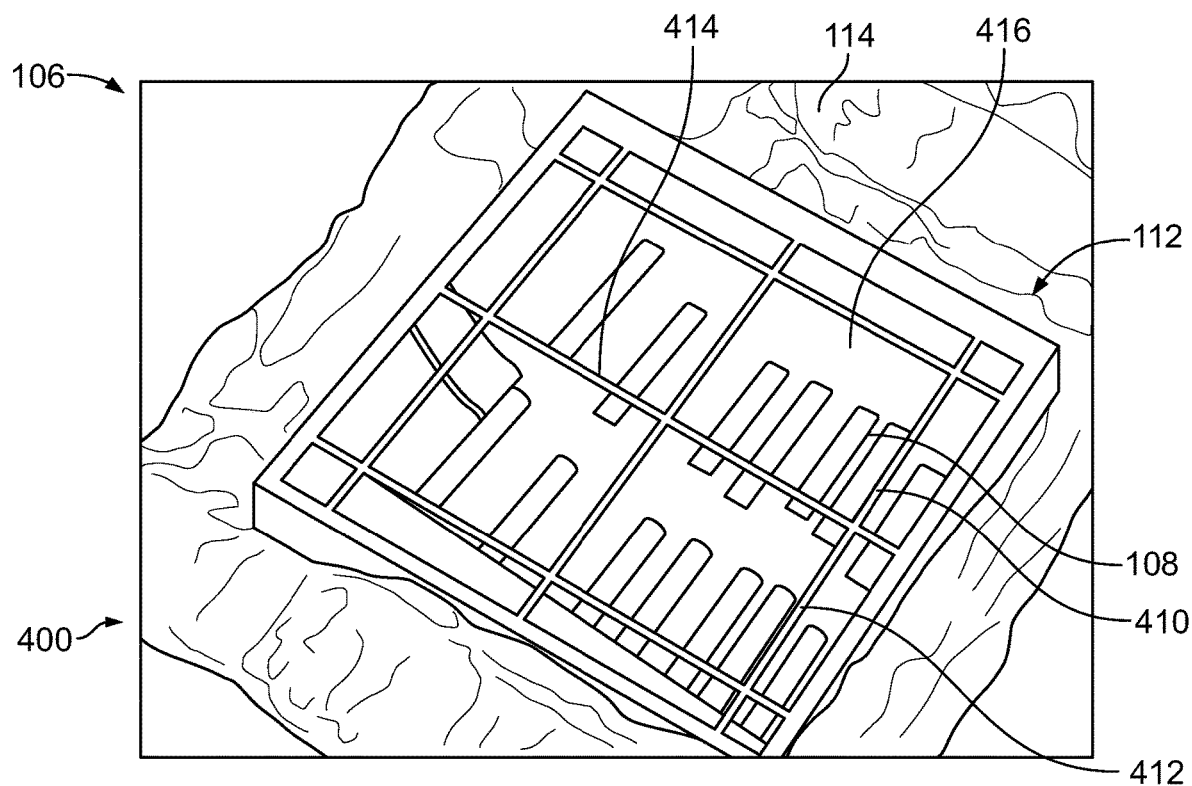
FIG. 28 illustrates a perspective bottom view of a sub-housing of the module of FIG. 27.

FIG. 28 illustrates a perspective bottom view of the sub-housing 400 of the module 106 of FIG. 27. In at least one embodiment, an EMI grid 410 is disposed within the aperture 112. The EMI grid 410 includes a plurality of longitudinal beams 412 that intersect a plurality of lateral beams 414, defining passages 416 therebetween. The beams 412 and 414 may have a thickness between 0.001"-0.010", for example. In this manner, the EMI grid 410 can be a mesh screen or cage, for example. The EMI grid 410 also hinders passage of EMI into or out of the module 106. In at least one embodiment, the EMI grid 410 can be formed of stainless steel. Alternatively, the module 106 does not include the EMI grid 410.

Figure 29:
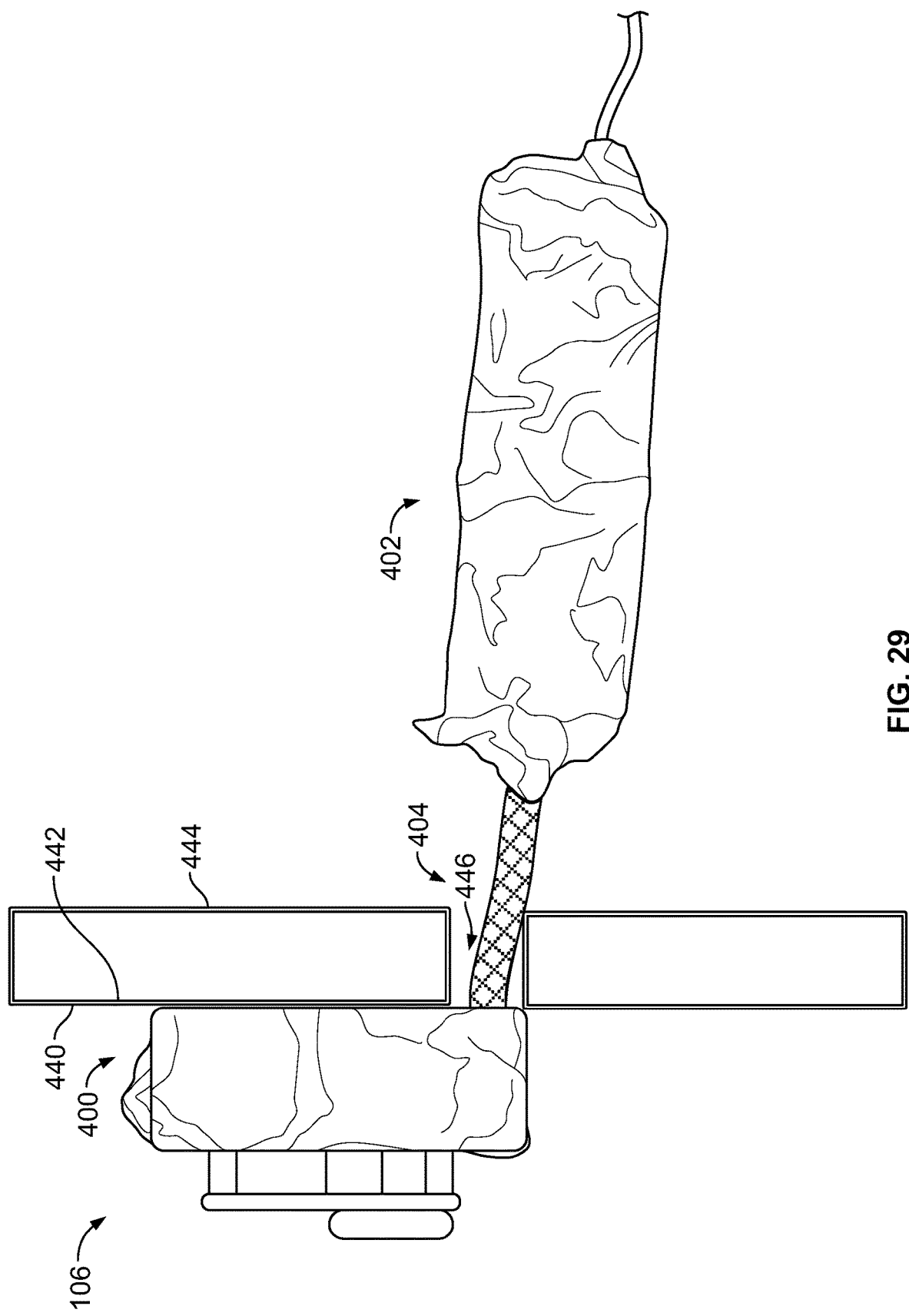
FIG. 29 illustrates a lateral view of the module of FIG. 27 secured to a wall, according to an embodiment of the present disclosure.

FIG. 29 illustrates a lateral view of the module 106 of FIG. 27 secured to a wall 440, according to an embodiment of the present disclosure. The sub-housing 400 can be mounted on a first surface 442 (such as an outer or inner surface) of the wall 440, and the power supply 402 can be disposed behind the wall 440. For example, the power supply 402 can be secured behind a second surface 444 (opposite from the first surface) of the wall 440. An opening 446 formed through the wall 440 is configured to allow the cable 404 to pass therethrough. In this manner, the wall 440 also isolates the sub-housing 400 from the power supply 402.

The wall 440 may be a portion of a room. For example, the wall 440 may be a wall of a lavatory, such as the lavatory 220 shown in FIGS. 18, 19, 23, and 24.

Figure 30:
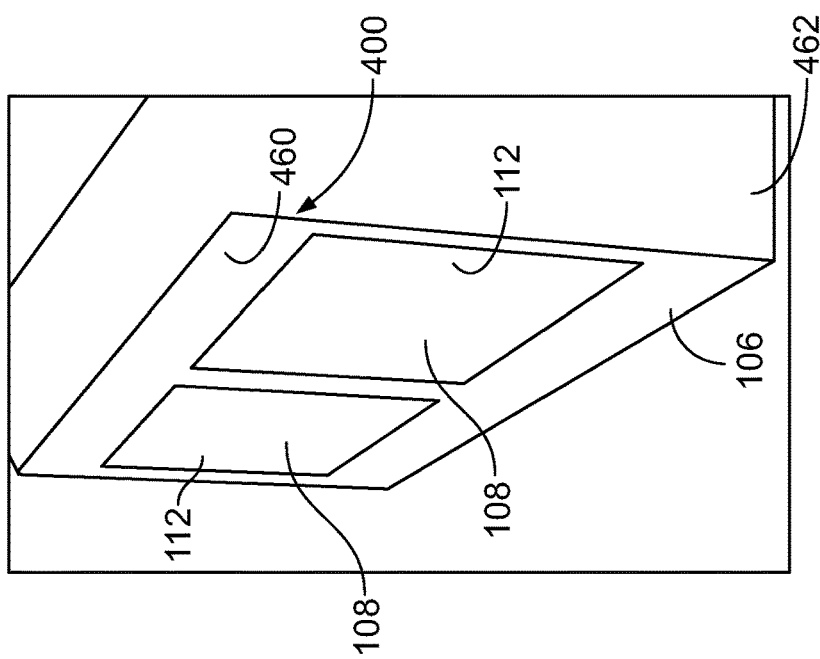
FIG. 30 illustrates a perspective front, lateral view of a module secured to a wall, according to an embodiment of the present disclosure.

FIG. 30 illustrates a perspective front, lateral view of the module 106 secured to the wall 440, according to an embodiment of the present disclosure. The sub-housing 400 may be secured to the wall 440 such that a front face 460, including the apertures 112, is flush with a front surface 462 of the wall 440.

Figure 31:
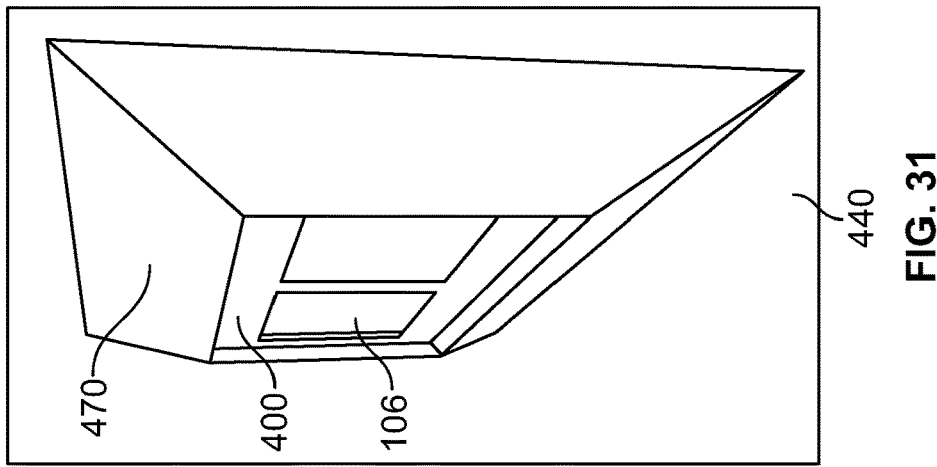
FIG. 31 illustrates a perspective front, lateral view of a module secured to a wall, according to an embodiment of the present disclosure.

FIG. 31 illustrates a perspective front, lateral view of the module 106 secured to the wall 440, according to an embodiment of the present disclosure. In this embodiment, the sub-housing 400 can be secured within a surrounding collar 470 that mounts the sub-housing 400 to the wall 440.

Figure 32:
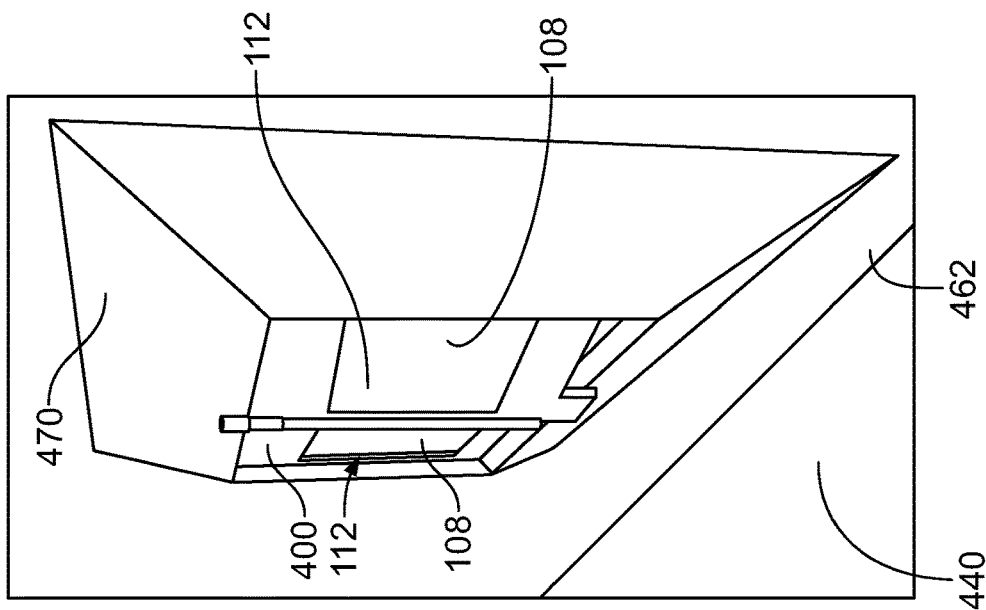
FIG. 32 illustrates a perspective front, lateral view of a module secured to a wall, according to an embodiment of the present disclosure.

FIG. 32 illustrates a perspective front, lateral view of the module 106 secured to the wall 440, according to an embodiment of the present disclosure. This embodiment is similar to that shown in FIG. 31, except that the apertures 112 may be angled (that is, not parallel) to the front surface 462 of the wall 440.

Figure 33:
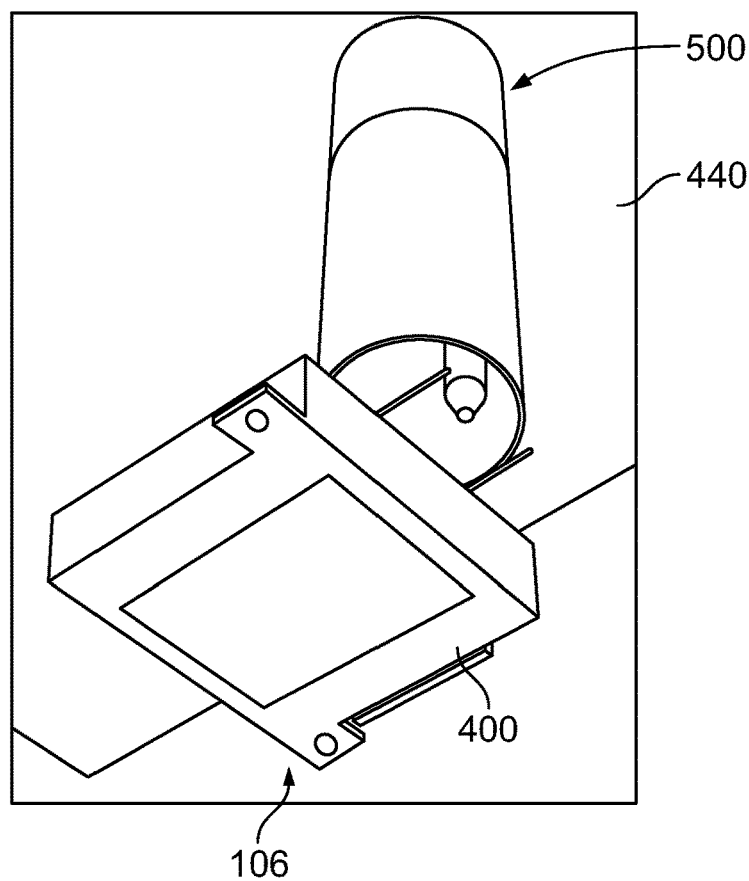
FIG. 33 illustrates a perspective front view of a module secured to a wall, according to an embodiment of the present disclosure.

FIG. 33 illustrates a perspective front view of the module 106 secured to the wall 440, according to an embodiment of the present disclosure. In this embodiment, a shielding shroud 500, such as a metal cylinder, is secured to and/or behind the wall 440. The power supply 402 (shown in FIG. 29, for example) is retained within the shielding shroud 500. In this embodiment, the shielding shroud 500 provides the EMI shielding for the power supply 402. Additional EMI shielding, such as in the form of a metal foil, may nor may not extend around the power supply 402 within the shielding shroud 500.

In at least one embodiment, the shielding shroud 500 is configured to fit into and be retained within an opening formed in the wall 440. As such, the shielding shroud 500 can be easily installed into the wall 440.

Figure 34:
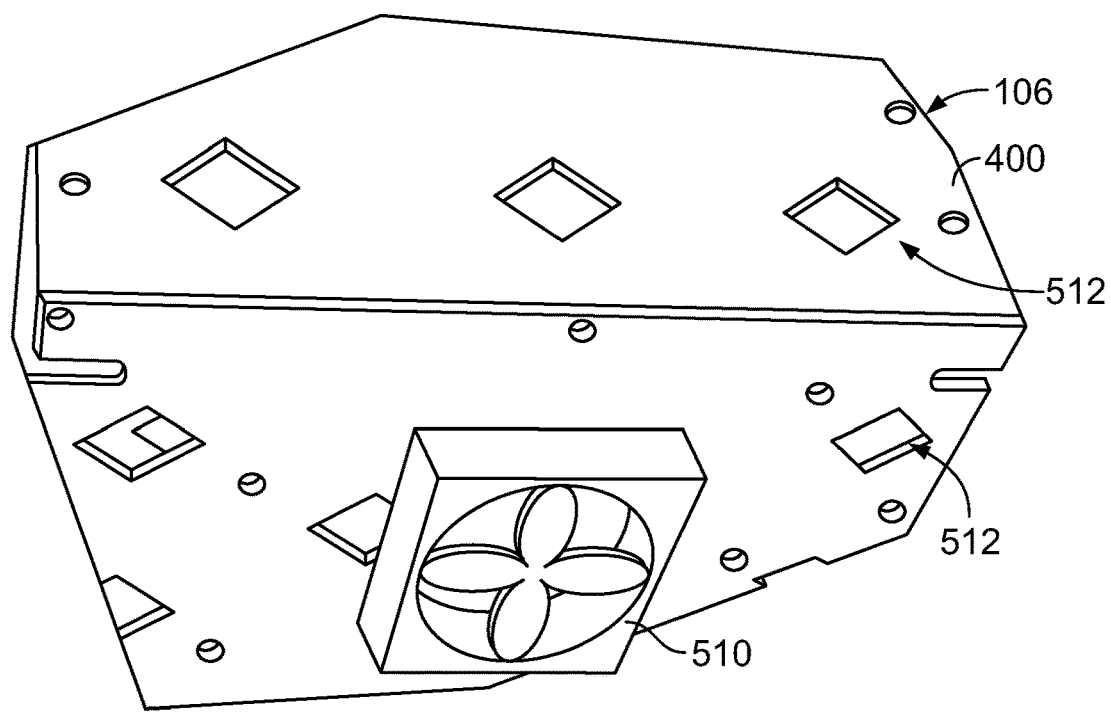
FIG. 34 illustrates a perspective rear view of a sub-housing of a module, according to an embodiment of the present disclosure.

FIG. 34 illustrates a perspective rear view of the sub-housing 400 of the module 106, according to an embodiment of the present disclosure. As shown, the sub-housing 400 may include a cooling fan 510 and a plurality of ventilation openings 512. The cooling fan 510 operates to cool the UV light emitters 108 during operation, and the ventilation openings 512 draw in cooling air and/or allow air within the sub-housing 400 to pass therethrough. The cooling fan 510 and the ventilation openings 512 may be used with any of the embodiments described herein. In embodiments in which an EMI shield covers portions of the sub-housing 400, the EMI shield does not cover the cooling fan 510 and the ventilation openings 512.

The ventilation openings 512 can be sized and shaped depending on EMI wavelength requirements. For example, in at least one embodiment, the ventilation openings 512 can be between 0.5"-1.0".

Figure 35:
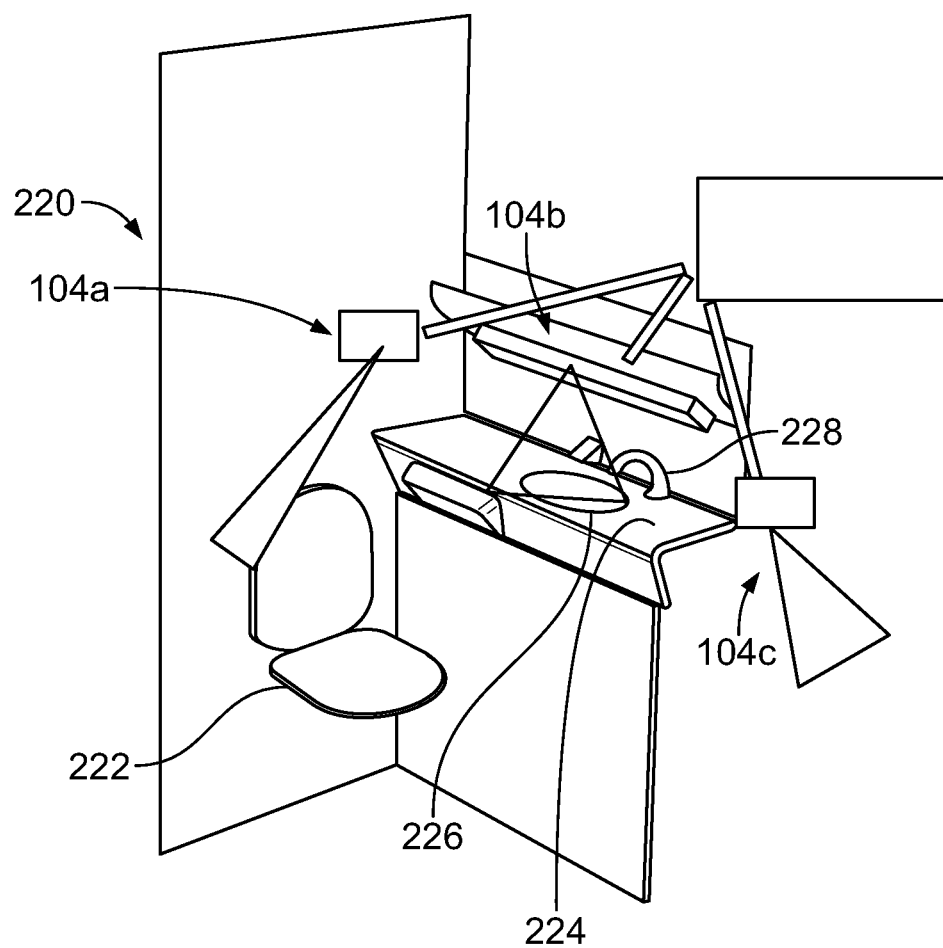
FIG. 35 illustrates a perspective internal view of a lavatory, according to an embodiment of the present disclosure.

FIG. 35 illustrates a perspective internal view of the lavatory 220, according to an embodiment of the present disclosure. The lavatory 220 can include a plurality of UV lamps, according to any of the embodiments described herein. For example, a first UV lamp 104a is configured to emit UV light onto a flush handle of the toilet 222. A second UV lamp 104b is configured to emit UV light onto the counter 224, including the sink 226 and the faucet 228. A third UV lamp 104c is configured to emit UV light onto a door handle, for example. The lavatory 220 can include more or less UV lamps than shown.

Figure 36:
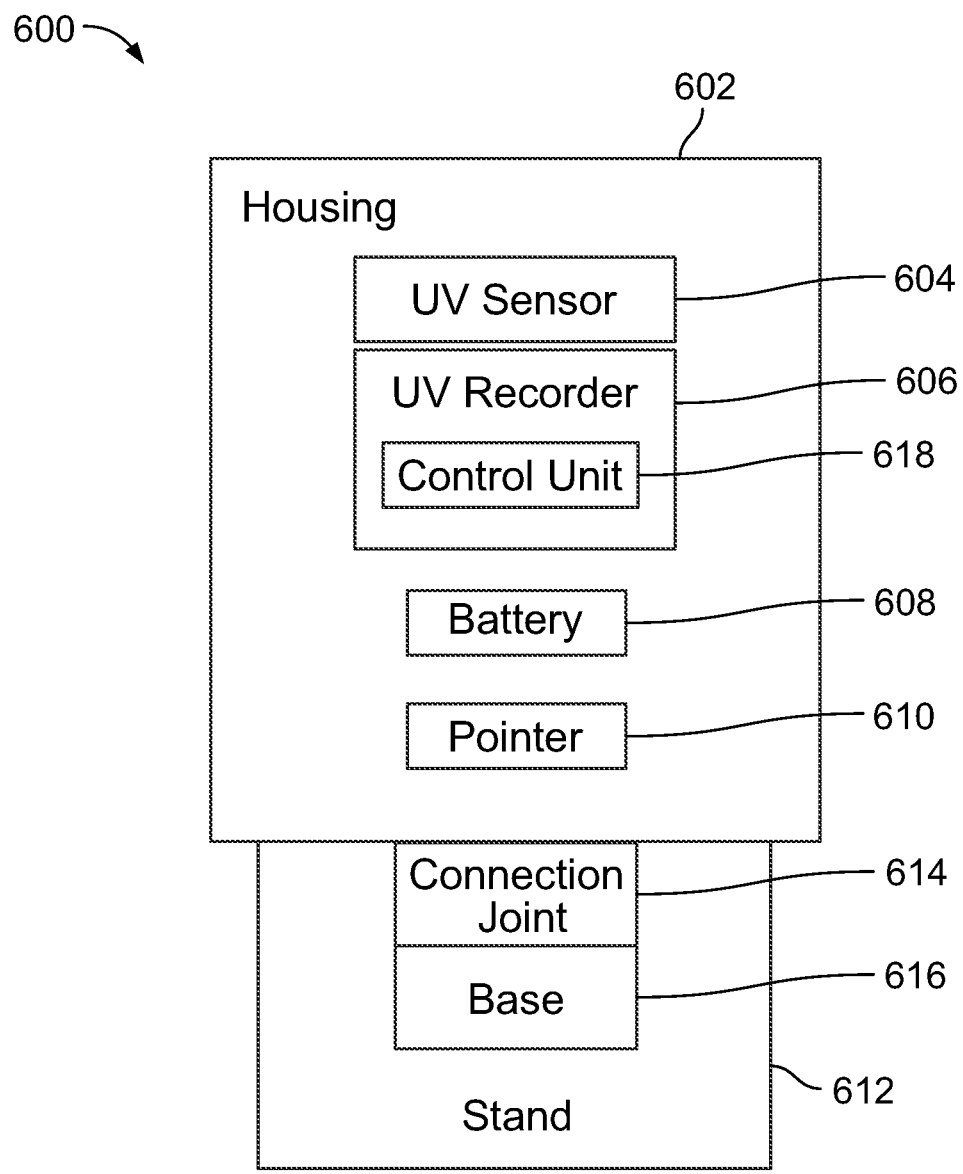
FIG. 36 illustrates a schematic block diagram of an alignment system for verifying a desired alignment of an ultraviolet (UV) lamp with respect to a target component, according to an embodiment of the present disclosure.

FIG. 36 illustrates a schematic block diagram of an alignment system 600 for verifying a desired alignment of an ultraviolet (UV) lamp with respect to a target component, according to an embodiment of the present disclosure. The UV lamp can be a contiguous UV lamp (that is, not formed from a plurality of modules) including one or more UV light emitters, as described with respect to FIG. 1, for example. Optionally, the UV lamp can be formed from modules, as described herein.

The alignment system 600 includes a housing 602. The housing 602 retains a UV sensor 604, a UV recorder 606, a battery 608, and a pointer 610. In at least one embodiment, the housing 602 is coupled to a stand 612 that includes a connection joint 614 that adjustably connects a base 616 of the stand 612 to the housing 602.

The UV sensor 604 is configured to detect UV light. In at least one embodiment, the UV sensor 604 includes one or more photodiodes that are configured to detect UV light. Optionally, the UV sensor 604 can include a low pass filter that is configured to filter out all optical light and only allow detection of UV light. The UV sensor 604 is communicatively coupled to the UV recorder 606, such as through one or more wired or wireless connections. In at least one embodiment, the UV recorder 606 includes a control unit 618 that receives signals indicative of sensed UV light from the UV sensor 604, and records information regarding the UV light in a memory, for example.

The battery 608 provides power to the UV sensor 604 and the UV recorder 606. In at least one embodiment, the battery 608 is rechargeable. Optionally, the alignment system 600 can include an electrical plug, in addition to or in place of the battery 608. The electrical plug allows the alignment system to be coupled to another source of power, such as a source of alternating current (AC) power.

The pointer 610 is movable in relation to the housing 602. The pointer 610 is configured to be linearly moved between a retracted position and an extended position. In at least one embodiment, the pointer 610 is a telescoping arm including telescoping segments. As another example, the pointer 610 includes slidable members that linearly slide in relation to one another. As another example, the pointer 610 includes an articulating arm that is configured to extend into a fully linear position.

The connection joint 614 allows the housing 602 to be moved relative to the stand 612. In at least one embodiment, the connection joint 614 is or includes a ball joint. As another example, the connection joint 614 can include one or more articulating or pivoting arms.

The base 616 can include a securing member that securely fixes the alignment system 600 to a surface. For example, the base 616 can include a suction cup, tape (single or double sided), and/or the like. Alternatively, the alignment system 600 may not include the stand 612.

The alignment system 600 ensures proper alignment of a UV lamp, such as in a space that is to be unoccupied during testing. The UV lamp is aligned to ensure a proper UV illumination with respect to a target component (that is, a component that is to be disinfected by UV light emitted by the UV lamp). The alignment system 600 allows an individual to leave a room having the UV lamp while the alignment system 600 validates that the UV light emitter(s) of the UV lamp are in a desired alignment to provide a desired UV radiance in relation to the target component.

The alignment system 600 allows for the UV lamp to be aligned as desired after a first test, in contrast to a trial and error approach. As such, the alignment system 600 reduces installation and testing times, and improves disinfecting UV irradiance in relation to the target component.

As described herein, the alignment system 600 is configured to verify a desired alignment of an ultraviolet (UV) lamp with respect to a target component. The alignment system 600 includes the housing 602. The UV sensor 604 is coupled to the housing 602. The UV sensor 604 is configured to detect UV light emitted from one or more UV light sensors of the UV lamp and output one or more signals indicative of the UV light. The UV recorder 606 is coupled to the housing 602. The UV recorder 606 is in communication with the UV sensor 604. The UV recorder 606 is configured to receive the one or more signals from the UV sensor 604 and store data regarding the one or more signals.

In at least one embodiment, the pointer 610 extends from the housing 602. The pointer 610 is configured to assist in aligning the UV sensor 604 with the one or more UV light emitters. In at least one embodiment, the pointer 610 is movable between a retracted position and an extended position.

Figure 37:
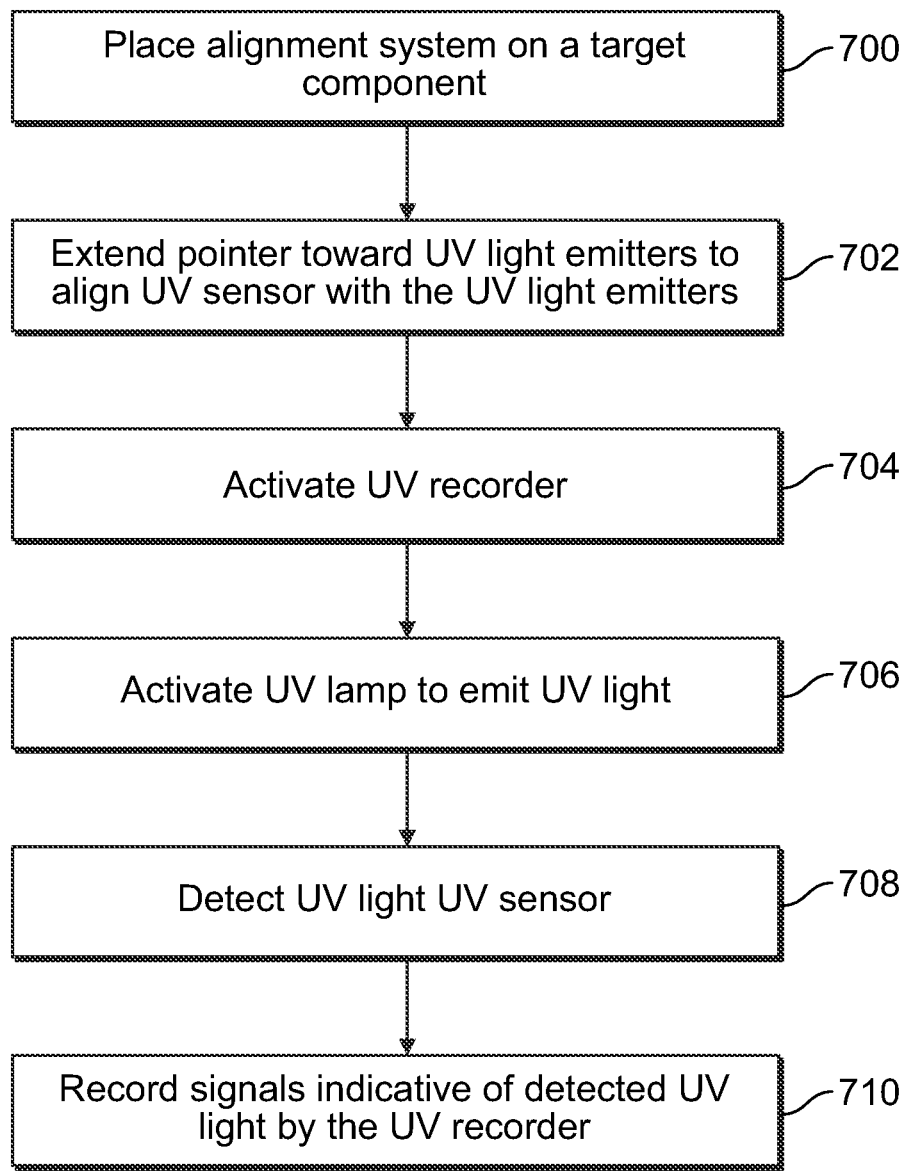
FIG. 37 illustrates a flow chart of an alignment method for verifying a desired alignment of a UV lamp, according to an embodiment of the present disclosure.

FIG. 37 illustrates a flow chart of an alignment method for verifying a desired alignment of a UV lamp, according to an embodiment of the present disclosure. Referring to FIGS. 36 and 37, the method begins at 700, at which the alignment system 600 is placed on a target component, such as a toilet, sink, door handle, countertop, wash basin, and/or the like. At 702, the pointer 610 is extended to ensure alignment of the UV sensor 604 with the UV light emitter(s) of the UV lamp. At 704, the UV recorder 606 is activated. The operator may then leave the space.

At 706, the UV lamp is activated to emit UV light from the UV light emitter(s). At 708, the UV sensor 604 detects the UV light, such as the intensity of the UV radiation. At 710, the UV recorder 606 records signals (received from the UV sensor) indicative of the detected UV light. In at least one embodiment, the UV sensor 604 detects the intensity of UV radiation and connects to the UV recorder 606 to output the electrical signal which varies with UV intensity. The UV recorder 606 stores data related to the detected UV light. The data can then be downloaded to a computing device, such as a laptop computer, a handheld smart device, a computer workstation, and/or the like. The operator may then analyze the data regarding the UV light stored in the recorder to validate the installation irradiance.

Figure 38:
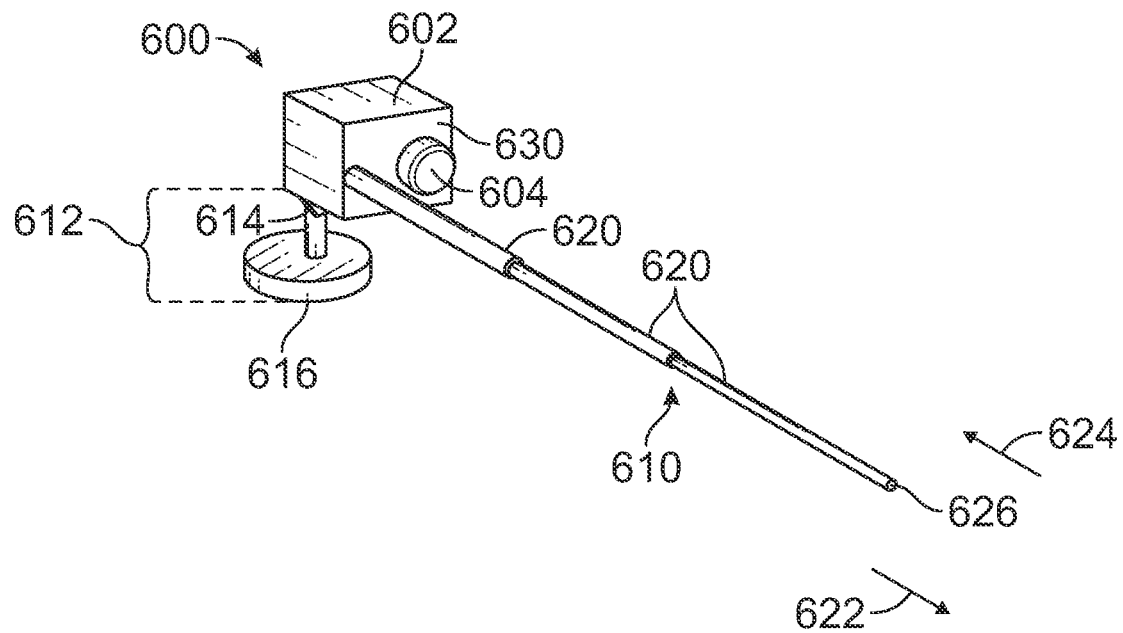
FIG. 38 illustrates a perspective front view of the alignment system having a pointer in an extended position, according to an embodiment of the present disclosure.
Figure 39:
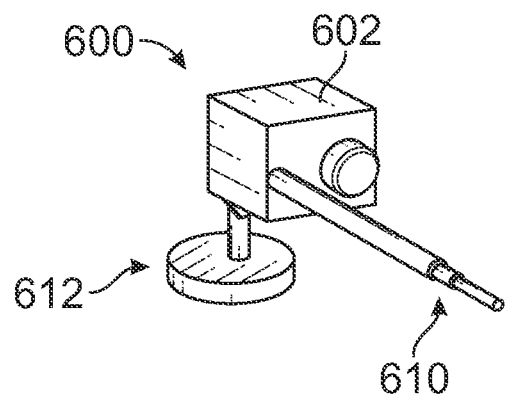
FIG. 39 illustrates a perspective front view of the alignment system of FIG. 38 having the pointer in a retracted position.

FIG. 38 illustrates a perspective front view of the alignment system 600 having a pointer 610 in an extended position, according to an embodiment of the present disclosure. FIG. 39 illustrates a perspective front view of the alignment system 600 of FIG. 38 having the pointer 610 in a retracted position. As shown in FIGS. 38 and 39, in at least one embodiment, the pointer 610 is a telescoping arm having a plurality of telescoping segments 620. The telescoping segments 620 are configured to allow the pointer 610 to linearly move in the directions of arrows 622 and 624. As the pointer 610 extends, the distal tip 626 of the pointer extends away from the housing 602 in the direction of arrow 622. As the pointer retracts, the distal tip 626 recedes toward the housing 602 in the direction of arrow 624.

In at least one embodiment, the housing 602 can be in the form of a block. Optionally, the housing 602 can be various other shapes, such as spherical, pyramidical, or the like. The UV sensor 604 includes a light-receiving portion 630, such as a lens, aperture, or the like, that extends outwardly from the housing 602. The UV recorder 606 and the battery 608 (shown in FIG. 36) may be disposed inside the housing 602.

Figure 40:
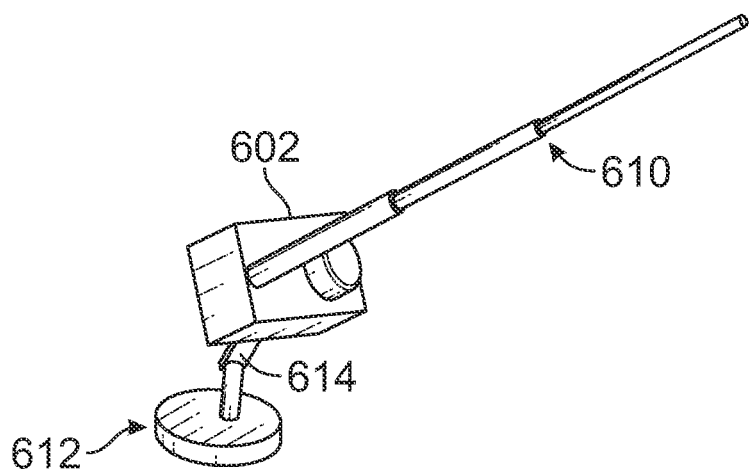
FIG. 40 illustrates a perspective front view of the alignment system of FIG. 38 having the housing pivoted into an upwardly-directed position.

FIG. 40 illustrates a perspective front view of the alignment system 600 of FIG. 38 having the housing 602 pivoted into an upwardly-directed position. The connection joint 614 allows the housing 602 to be moved relative to the stand 612 in various positions.

Optionally, the alignment system 600 may not include the stand 612 and/or the connection joint 614. In at least one embodiment, the alignment system 600 can be suspended in position, such as via a bracket, cables, or the like. In at least one other embodiment, the housing 602 can be set onto a surface without a stand.

Figure 41:
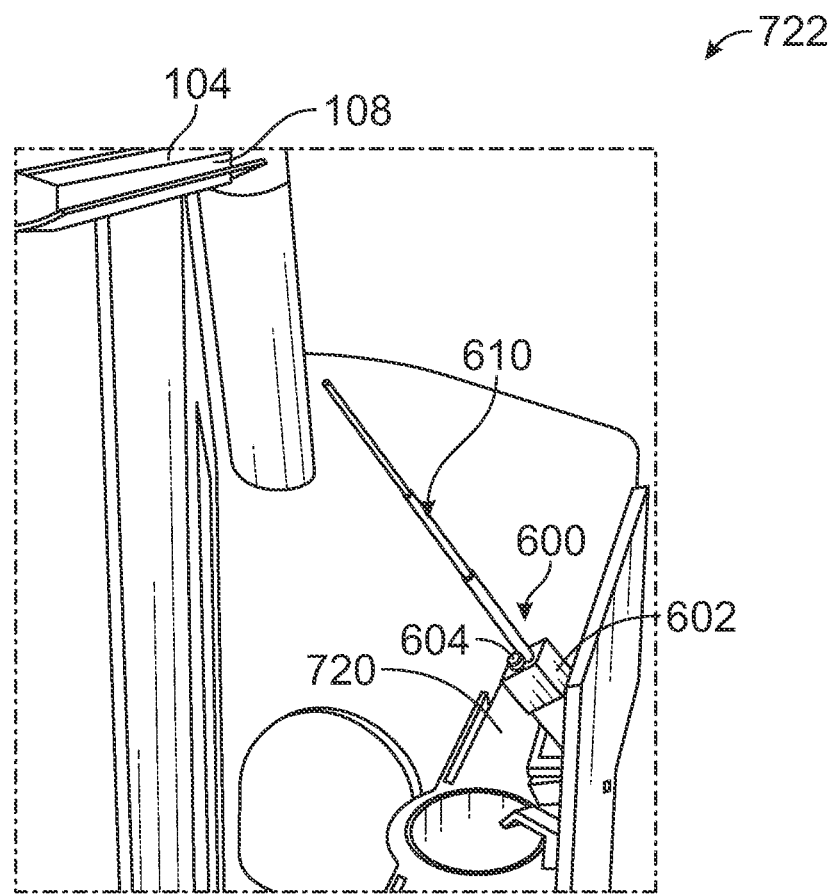
FIG. 41 illustrates a perspective view of the alignment system positioned on a target component within a lavatory, according to an embodiment of the present disclosure.

FIG. 41 illustrates a perspective view of the alignment system 600 positioned on a target component 720 within a lavatory 722, according to an embodiment of the present disclosure. The target component 720 can be a countertop. The target component 720 can be any structure within the lavatory 722 that is to be disinfected with UV light.

The lavatory 722 is an example of an enclosed space having a UV lamp 104. Embodiments of the present disclosure may be used with various other enclosed spaces. The alignment system 600 can be used in any space that includes a UV lamp 104, such as a galley, flight deck, office, residential room, and/or the like, whether or not the UV lamp 104 is prevented from emitting UV light when the space is occupied.

As shown, the housing 602 is moved so that the UV sensor 604 is facing the UV light emitter(s) 108 of the UV lamp 104. The pointer 610 is then extended to ensure precise alignment between the UV light emitter(s) 108 and the UV sensor 604.

Figure 42:
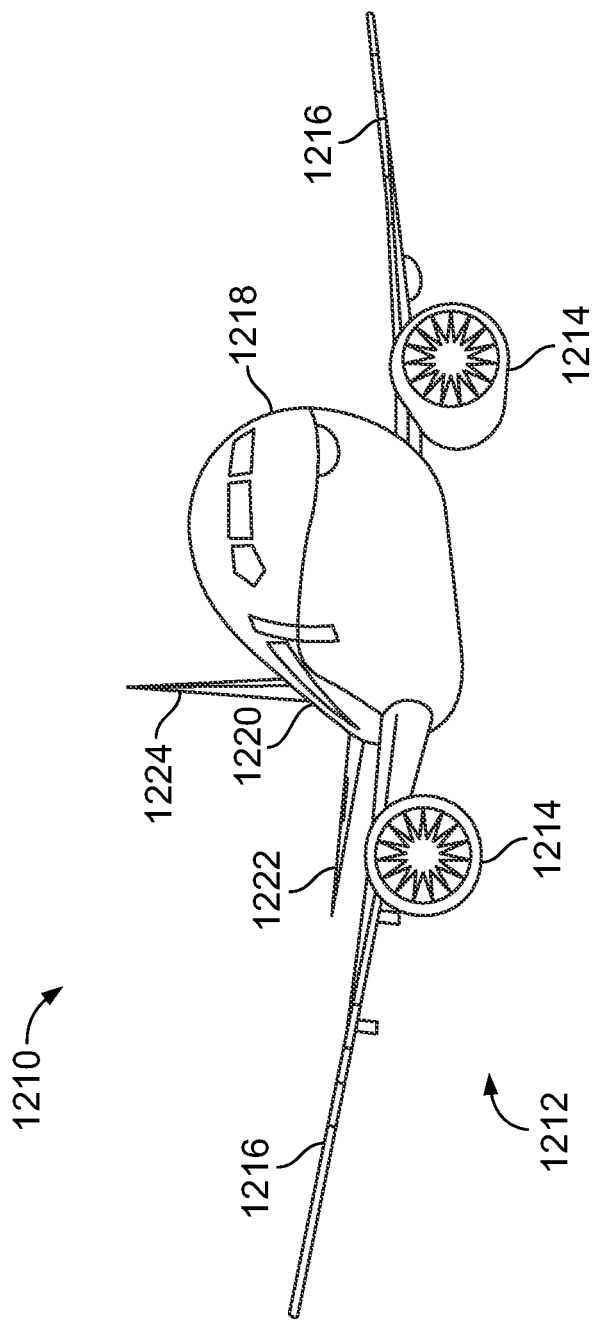
FIG. 42 illustrates a perspective front view of an aircraft, according to an embodiment of the present disclosure.

FIG. 42 illustrates a perspective front view of an aircraft 1210, according to an embodiment of the present disclosure. The aircraft 1210 includes a propulsion system 1212 that includes engines 1214, for example. Optionally, the propulsion system 1212 may include more engines 1214 than shown. The engines 1214 are carried by wings 1216 of the aircraft 1210. In other embodiments, the engines 1214 may be carried by a fuselage 1218 and/or an empennage 1220. The empennage 1220 may also support horizontal stabilizers 1222 and a vertical stabilizer 1224.

The fuselage 1218 of the aircraft 1210 defines an internal cabin 1230, which includes a flight deck or cockpit, one or more work sections (for example, galleys, personnel carry-on baggage areas, and the like), one or more passenger sections (for example, first class, business class, and coach sections), one or more lavatories, and/or the like.

Embodiments of the present disclosure are used to disinfect various components within the internal cabin 1230. Alternatively, instead of an aircraft, embodiments of the present disclosure may be used with various other vehicles, such as automobiles, buses, locomotives and train cars, watercraft, and the like. Further, embodiments of the present disclosure may be used with respect to fixed structures, such as commercial and residential buildings.

Figure 43A:
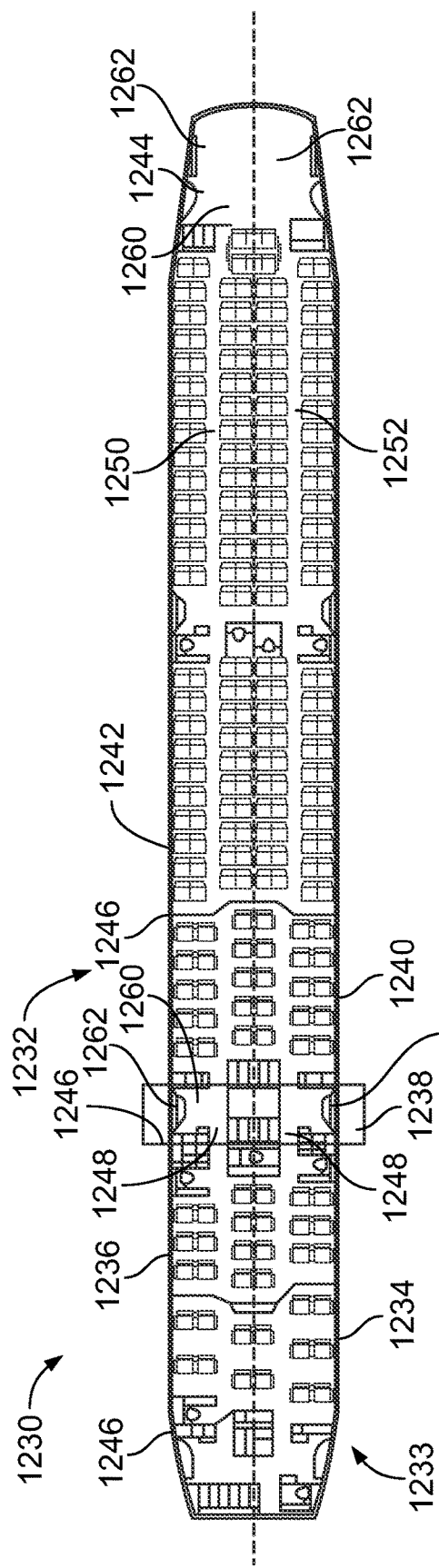
FIG. 43A illustrates a top plan view of an internal cabin of an aircraft, according to an embodiment of the present disclosure.

FIG. 43A illustrates a top plan view of an internal cabin 1230 of an aircraft, according to an embodiment of the present disclosure. The internal cabin 1230 may be within the fuselage 1232 of the aircraft, such as the fuselage 1218 of FIG. 42. For example, one or more fuselage walls may define the internal cabin 1230. The internal cabin 1230 includes multiple sections, including a front section 1233, a first class section 1234, a business class section 1236, a front galley station 1238, an expanded economy or coach section 1240, a standard economy of coach section 1242, and an aft section 1244, which may include multiple lavatories and galley stations. It is to be understood that the internal cabin 1230 may include more or less sections than shown. For example, the internal cabin 1230 may not include a first class section, and may include more or less galley stations than shown. Each of the sections may be separated by a cabin transition area 1246, which may include class divider assemblies between aisles 1248.

As shown in FIG. 43A, the internal cabin 1230 includes two aisles 1250 and 1252 that lead to the aft section 1244. Optionally, the internal cabin 1230 may have less or more aisles than shown. For example, the internal cabin 1230 may include a single aisle that extends through the center of the internal cabin 1230 that leads to the aft section 1244.

The aisles 1248, 1250, and 1252 extend to egress paths or door passageways 1260. Exit doors 1262 are located at ends of the egress paths 1260. The egress paths 1260 may be perpendicular to the aisles 1248, 1250, and 1252. The internal cabin 1230 may include more egress paths 1260 at different locations than shown. Embodiments of the present disclosure shown and described with respect to FIGS. 1-41 may be used to sanitize various structures within the internal cabin 1230, such as passenger seats, monuments, stowage bin assemblies, components on and within lavatories, galley equipment and components, and/or the like.

Figure 43B:
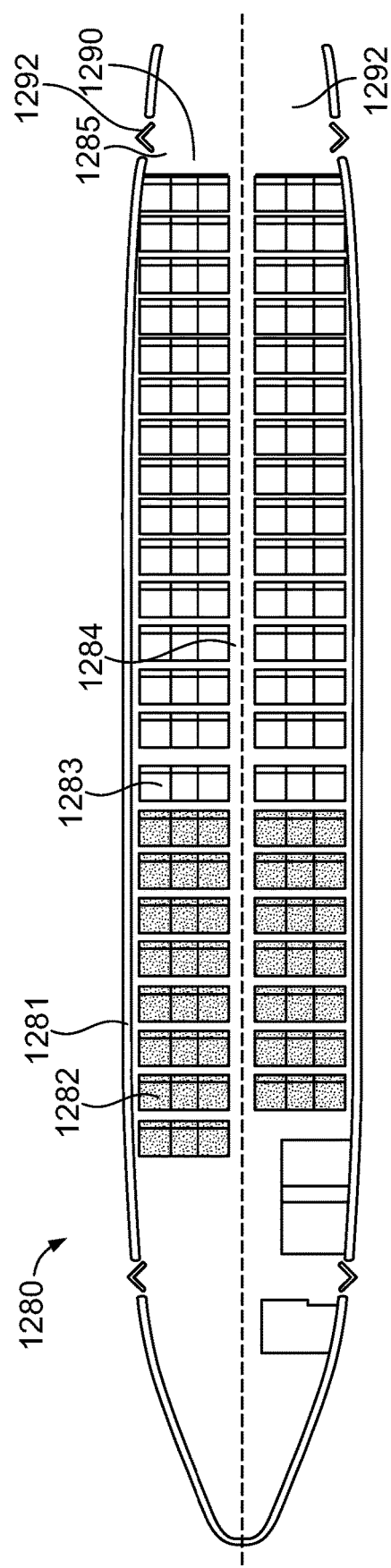
FIG. 43B illustrates a top plan view of an internal cabin of an aircraft, according to an embodiment of the present disclosure.

FIG. 43B illustrates a top plan view of an internal cabin 1280 of an aircraft, according to an embodiment of the present disclosure. The internal cabin 1280 is an example of the internal cabin 1230 shown in FIG. 30. The internal cabin 1280 may be within a fuselage 1281 of the aircraft. For example, one or more fuselage walls may define the internal cabin 1280. The internal cabin 1280 includes multiple sections, including a main cabin 1282 having passenger seats 1283, and an aft section 1285 behind the main cabin 1282. It is to be understood that the internal cabin 1280 may include more or less sections than shown.

The internal cabin 1280 may include a single aisle 1284 that leads to the aft section 1285. The single aisle 1284 may extend through the center of the internal cabin 1280 that leads to the aft section 1285. For example, the single aisle 1284 may be coaxially aligned with a central longitudinal plane of the internal cabin 1280.

The aisle 1284 extends to an egress path or door passageway 1290. Exit doors 1292 are located at ends of the egress path 1290. The egress path 1290 may be perpendicular to the aisle 1284. The internal cabin 1280 may include more egress paths than shown. Embodiments of the present disclosure shown and described with respect to FIGS. 1-41 may be used to sanitize various structures within the internal cabin 1230, such as passenger seats, monuments, stowage bin assemblies, components on and within lavatories, galley equipment and components, and/or the like.

Figure 44:
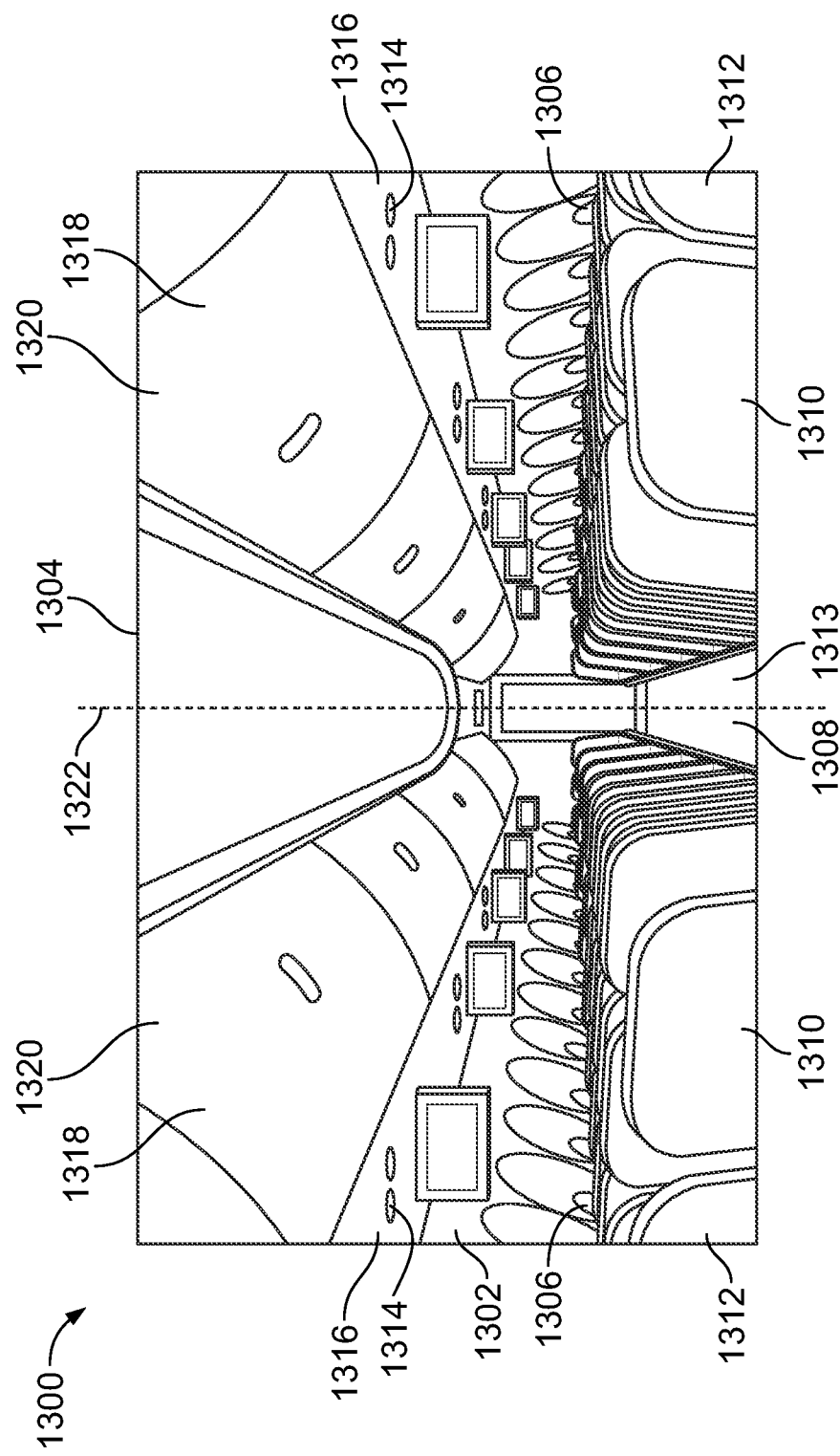
FIG. 44 illustrates a perspective interior view of an internal cabin of an aircraft, according to an embodiment of the present disclosure.

FIG. 44 illustrates a perspective interior view of an internal cabin 1300 of an aircraft, according to an embodiment of the present disclosure. The internal cabin 1300 includes outboard walls 1302 connected to a ceiling 1304. Windows 1306 may be formed within the outboard walls

1302. A floor 1308 supports rows of seats 1310. As shown in FIG. 44, a row 1312 may include two seats 1310 on either side of an aisle 1313. However, the row 1312 may include more or less seats 1310 than shown. Additionally, the internal cabin 1300 may include more aisles than shown.

Passenger service units (PSUs) 1314 are secured between an outboard wall 1302 and the ceiling 1304 on either side of the aisle 1313. The PSUs 1314 extend between a front end and rear end of the internal cabin 1300. For example, a PSU 1314 may be positioned over each seat 1310 within a row 1312. Each PSU 1314 may include a housing 1316 that generally contains vents, reading lights, an oxygen bag drop panel, an attendant request button, and other such controls over each seat 1310 (or groups of seats) within a row 1312.

Overhead stowage bin assemblies 1318 are secured to the ceiling 1304 and/or the outboard wall 1302 above and inboard from the PSU 1314 on either side of the aisle 1313. The overhead stowage bin assemblies 1318 are secured over the seats 1310. The overhead stowage bin assemblies 1318 extend between the front and rear end of the internal cabin 1300. Each stowage bin assembly 1318 may include a pivot bin or bucket 1320 pivotally secured to a strongback (hidden from view in FIG. 44). The overhead stowage bin assemblies 1318 may be positioned above and inboard from lower surfaces of the PSUs 1314. The overhead stowage bin assemblies 1318 are configured to be pivoted open in order to receive passenger carry-on baggage and personal items, for example.

As used herein, the term "outboard" means a position that is further away from a central longitudinal plane 1322 of the internal cabin 1300 as compared to another component. The term "inboard" means a position that is closer to the central longitudinal plane 1322 of the internal cabin 1300 as compared to another component. For example, a lower surface of a PSU 1314 may be outboard in relation to a stowage bin assembly 1318.

Embodiments of the present disclosure shown and described with respect to FIGS. 1-41 may be used to sanitize various structures shown within the internal cabin 1300.

As described herein, certain embodiments of the present disclosure provide systems and methods that allow for efficient production and maintenance of a UV lamp. Further, certain embodiments of the present disclosure provide systems and methods that ensures that UV light disinfection of one or more components within an area occurs when the area is unoccupied. Also, certain embodiments of the present disclosure provide systems and methods reduce EMI emanating from UV light emitters.

Additionally, embodiments of the present disclosure provide systems and methods of aligning a UV lamp within a setting that may not allow for an individual to be present.

Further, the disclosure comprises embodiments according to the following clauses:

Clause 1. A system for verifying a desired alignment of an ultraviolet (UV) lamp with respect to a target component, the system comprising:
  a housing;
  a UV sensor coupled to the housing, wherein the UV sensor is configured to detect UV light emitted from one or more UV light emitters of the UV lamp and output one or more signals indicative of the UV light; and
  a UV recorder coupled to the housing, wherein the UV recorder is in communication with the UV sensor, and wherein the UV recorder is configured to receive the one or more signals from the UV sensor and store data regarding the one or more signals.

Clause 2. The system of Clause 1, further comprising a pointer extending from the housing, wherein the pointer is configured to assist in aligning the UV sensor with the one or more UV light emitters.

Clause 3. The system of Clause 2, wherein the pointer is movable between a retracted position and an extended position.

Clause 4. The system of Clause 3, wherein the pointer is configured to linearly move between the retracted position and the extended position.

Clause 5. The system of Clauses 3 or 4, wherein the pointer is a telescoping arm having a plurality of telescoping segments.

Clause 6. The system of any of Clauses 1-5, further comprising a battery.

Clause 7. The system of any of Clauses 1-6, further comprising a stand connected to the housing.

Clause 8. The system of Clause 7, wherein the stand comprises:
  a base; and
  a connection joint that connects to the housing, wherein the connection joint allows the housing to move relative to the stand.

Clause 9. The system of any of Clauses 1-8, wherein the UV recorder comprises a control unit that receives the one or more signals.

Clause 10. A method for verifying a desired alignment of an ultraviolet (UV) lamp with respect to a target component, the method comprising:
  detecting, by a UV sensor coupled to a housing, UV light emitted from one or more UV light emitters of the UV lamp;
  outputting, by the UV sensor, one or more signals indicative of the UV light;
  receiving, by a UV recorder coupled to the housing and in communication with the UV sensor, the one or more signals from the UV sensor; and
  storing, by the UV record, data regarding the one or more signals.

Clause 11. The method of Clause 10, further comprising using a pointer extending from the housing to assist in aligning the UV sensor with the one or more UV light emitters.

Clause 12. The method of Clause 11, further comprising moving the pointer between a retracted position and an extended position.

Clause 13. The method of Clause 12, wherein said moving comprises linearly moving the pointer between the retracted position and the extended position.

Clause 14. The method of any of Clauses 10-13, further comprising moving the housing relative to a stand connected to the housing.

Clause 15. An enclosed space comprising:
  a target component;
  an ultraviolet (UV) lamp including one or more UV light emitters; and
  a system for verifying a desired alignment of the UV lamp with respect to the target component, the system comprising:
    a housing;
    a UV sensor coupled to the housing, wherein the UV sensor is configured to detect UV light emitted from the one or more UV light emitters of the UV lamp and output one or more signals indicative of the UV light; and
    a UV recorder coupled to the housing, wherein the UV recorder is in communication with the UV sensor, and wherein the UV recorder is configured to receive the one or more signals from the UV sensor and store data regarding the one or more signals.

Clause 16. The enclosed space of Clause 15, wherein the system further comprises a pointer extending from the housing, wherein the pointer is configured to assist in aligning the UV sensor with the one or more UV light emitters.

Clause 17. The enclosed space of Clause 16, wherein the pointer is movable between a retracted position and an extended position, wherein the pointer is configured to linearly move between the retracted position and the extended position, and wherein the pointer is a telescoping arm having a plurality of telescoping segments.

Clause 18. The enclosed space of any of Clauses 15-17, wherein the system further comprises a stand connected to the housing.

Clause 19. The enclosed space of Clause 18, wherein the stand comprises:
 a base; and
 a connection joint that connects to the housing, wherein the connection joint allows the housing to move relative to the stand.

Clause 20. The enclosed space of any of Clauses 15-19, wherein the UV recorder comprises a control unit that receives the one or more signals.

While various spatial and directional terms, such as top, bottom, lower, mid, lateral, horizontal, vertical, front and the like can be used to describe embodiments of the present disclosure, it is understood that such terms are merely used with respect to the orientations shown in the drawings. The orientations can be inverted, rotated, or otherwise changed, such that an upper portion is a lower portion, and vice versa, horizontal becomes vertical, and the like.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein.

It is to be understood that the above description is intended to be illustrative, and not restrictive. For example, the above-described embodiments (and/or aspects thereof) can be used in combination with each other. In addition, many modifications can be made to adapt a particular situation or material to the teachings of the various embodiments of the disclosure without departing from their scope. While the dimensions and types of materials described herein are intended to define the parameters of the various embodiments of the disclosure, the embodiments are by no means limiting and are exemplary embodiments. Many other embodiments will be apparent to those of skill in the art upon reviewing the above description. The scope of the various embodiments of the disclosure should, therefore, be determined with reference to the appended claims, along with the full scope of equivalents to which such claims are entitled. In the appended claims and the detailed description herein, the terms "including" and "in which" are used as the plain-English equivalents of the respective terms "comprising" and "wherein." Moreover, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various embodiments of the disclosure, including the best mode, and also to enable any person skilled in the art to practice the various embodiments of the disclosure, including making and using any devices or systems and performing any incorporated methods. The patentable scope of the various embodiments of the disclosure is defined by the claims, and can include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. A system for verifying a desired alignment of an ultraviolet (UV) lamp with respect to a target component, the system comprising:
 a housing;
 a UV sensor coupled to the housing, wherein the UV sensor is configured to detect UV light emitted from one or more UV light emitters of the UV lamp and output one or more signals indicative of the UV light; and
 a UV recorder coupled to the housing, wherein the UV recorder is in communication with the UV sensor, and wherein the UV recorder is configured to receive the one or more signals from the UV sensor and store data regarding the one or more signals.

2. The system of claim 1, further comprising a pointer extending from the housing, wherein the pointer is configured to assist in aligning the UV sensor with the one or more UV light emitters.

3. The system of claim 2, wherein the pointer is movable between a retracted position and an extended position.

4. The system of claim 3, wherein the pointer is configured to linearly move between the retracted position and the extended position.

5. The system of claim 3, wherein the pointer is a telescoping arm having a plurality of telescoping segments.

6. The system of claim 1, further comprising a battery.

7. The system of claim 1, further comprising a stand connected to the housing.

8. The system of claim 7, wherein the stand comprises:
 a base; and
 a connection joint that connects to the housing, wherein the connection joint allows the housing to move relative to the stand.

9. The system of claim 1, wherein the UV recorder comprises a control unit that receives the one or more signals.

10. A method for verifying a desired alignment of an ultraviolet (UV) lamp with respect to a target component, the method comprising:
 detecting, by a UV sensor coupled to a housing, UV light emitted from one or more UV light emitters of the UV lamp;
 outputting, by the UV sensor, one or more signals indicative of the UV light;
 receiving, by a UV recorder coupled to the housing and in communication with the UV sensor, the one or more signals from the UV sensor; and
 storing, by the UV record, data regarding the one or more signals.

11. The method of claim 10, further comprising using a pointer extending from the housing to assist in aligning the UV sensor with the one or more UV light emitters.

12. The method of claim 11, further comprising moving the pointer between a retracted position and an extended position.

13. The method of claim 12, wherein said moving comprises linearly moving the pointer between the retracted position and the extended position.

14. The method of claim 10, further comprising moving the housing relative to a stand connected to the housing.

15. An enclosed space comprising:
   a target component;
   an ultraviolet (UV) lamp including one or more UV light emitters; and
   a system for verifying a desired alignment of the UV lamp with respect to the target component, the system comprising:
      a housing;
      a UV sensor coupled to the housing, wherein the UV sensor is configured to detect UV light emitted from the one or more UV light emitters of the UV lamp and output one or more signals indicative of the UV light; and
      a UV recorder coupled to the housing, wherein the UV recorder is in communication with the UV sensor, and wherein the UV recorder is configured to receive the one or more signals from the UV sensor and store data regarding the one or more signals.

16. The enclosed space of claim 15, wherein the system further comprises a pointer extending from the housing, wherein the pointer is configured to assist in aligning the UV sensor with the one or more UV light emitters.

17. The enclosed space of claim 16, wherein the pointer is movable between a retracted position and an extended position, wherein the pointer is configured to linearly move between the retracted position and the extended position, and wherein the pointer is a telescoping arm having a plurality of telescoping segments.

18. The enclosed space of claim 15, wherein the system further comprises a stand connected to the housing.

19. The enclosed space of claim 18, wherein the stand comprises:
   a base; and
   a connection joint that connects to the housing, wherein the connection joint allows the housing to move relative to the stand.

20. The enclosed space of claim 15, wherein the UV recorder comprises a control unit that receives the one or more signals.

* * * * *